United States Patent
Liu et al.

(10) Patent No.: US 9,149,445 B2
(45) Date of Patent: Oct. 6, 2015

(54) INHIBITION OF GLYCEROL-3-PHOSPHATE ACYLTRANSFERASE (GPAT) AND ASSOCIATED ENZYMES FOR TREATMENT OF VIRAL INFECTIONS

(75) Inventors: Sean Liu, North Brunswick, NJ (US); Joshua D. Rabinowitz, Princeton, NJ (US); Thomas Shenk, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 772 days.

(21) Appl. No.: 13/387,452

(22) PCT Filed: Jul. 27, 2010

(86) PCT No.: PCT/US2010/043420
§ 371 (c)(1),
(2), (4) Date: Mar. 23, 2012

(87) PCT Pub. No.: WO2011/019498
PCT Pub. Date: Feb. 17, 2011

(65) Prior Publication Data
US 2012/0184600 A1 Jul. 19, 2012

Related U.S. Application Data

(60) Provisional application No. 61/228,815, filed on Jul. 27, 2009.

(51) Int. Cl.
*A61K 31/38* (2006.01)
*A61K 31/381* (2006.01)
*A61K 31/045* (2006.01)

(52) U.S. Cl.
CPC ............... *A61K 31/045* (2013.01); *A61K 31/38* (2013.01); *A61K 31/381* (2013.01)

(58) Field of Classification Search
CPC ............................. A61K 31/38; A61K 31/381
See application file for complete search history.

(56) References Cited

U.S. PATENT DOCUMENTS

2004/0033506 A1 2/2004 Farrelly et al.
2006/0247302 A1 11/2006 Kuhajda et al.

OTHER PUBLICATIONS

PCT International Search Report and Written Opinion for PCT/US10/43420 mailed on Nov. 18, 2010.
Munger et al., "Systems-level metabolic flux profiling identifies fatty acid synthesis as a target for antiviral therapy", Nature Biotechnology 2009, 26:1179-1186.

*Primary Examiner* — Yong Chong
(74) *Attorney, Agent, or Firm* — Kenyon & Kenyon LLP

(57) ABSTRACT

A method of treating or preventing a viral infection in a mammal by administering a compound or pharmaceutically acceptable derivative thereof that inhibits a phosphatidic acid synthesis enzyme.

6 Claims, 3 Drawing Sheets

INHIBITION OF GLYCEROL-3-PHOSPHATE ACYLTRANSFERASE (GPAT) AND ASSOCIATED ENZYMES FOR TREATMENT OF VIRAL INFECTIONS

CROSS-REFERENCE TO RELATED APPLICATIONS

This application is a national stage application of International Application No. PCT/US2010/043420, filed Jul. 27, 2010, which claims priority to U.S. Application No. 61/228,815, filed Jul. 27, 2009, which is incorporated herein by reference in its entirety.

STATEMENT OF GOVERNMENT INTEREST

This invention was made with government support under Grant No. R01 AI078063 and Grant No. 5 R01 CA085786 awarded by the National Institutes of Health. The government has certain rights in the invention.

FIELD OF THE INVENTION

The present invention provides methods and compounds for treating or preventing viral infections by modulating the activity of host cell enzymes to inhibit or reduce phosphatidic acid synthesis. Examples of such enzymes include glycerol-3-phosphate acyltransferase (GPAT), acylglycerol-3-phosphate acyltransferase (AGPAT), phospholipase D (PLD) and diacylglycerol kinase (DGK). The invention also provides pharmaceutical compositions for treating or preventing viral infections.

BACKGROUND OF THE INVENTION

There is a great unmet medical need for agents that more safely, effectively, and reliably treat viral infections, from HIV to the common cold. This includes a major need for better agents to treat human cytomegalovirus (where current agents suffer from significant toxicity and lack of efficacy), herpes simplex virus (where current agents are beneficial but provide incomplete relief), influenza A (where resistance to current agents is rampant), and hepatitis C virus (where many patients die from poor disease control). It further includes a major need for agents that work across a spectrum of viruses, facilitating their clinical use without necessarily requiring identification of the underlying pathogen.

SUMMARY OF THE INVENTION

The invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug.

In one embodiment, the compound is a compound of Formula I:

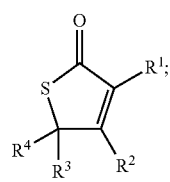

wherein
$R^1$ and $R^2$ are each independently —H, —OH, —OR$^5$, —OCH$_2$C(O)R$^5$, —OCH$_2$C(O)NHR$^5$, —OC(O)R$^5$, —OC(O)OR$^5$, —OC(O)NHNH—R$^5$, —OC(O)NR$^5$R$^6$, C$_1$-C$_{20}$ alkyl, cycloalkyl, alkenyl, alkynyl, aryl, arylalkyl, alkylaryl, —CHR$^5$OR$^6$, —CO(O)R$^5$, —C(O)NR$^5$R$^6$, —CH$_2$C(O)R$^5$, —CH$_2$C(O)NHR$^5$, —C(O)R$^5$, —CH$_2$OR$^5$, —C(O)R$^5$, —CO(O)R$^5$, —C(O)NR$^5$R$^6$, —CH$_2$C(O)R$^5$, or —CH$_2$C(O)NHR$^5$, $R^5$ and $R^6$ are each independently H, C$_1$-C$_{20}$ alkyl, cycloalkyl, alkenyl, alkynyl, aryl, arylalkyl, alkylaryl, or optionally contain halogen atoms;

$R^3$ and $R^4$, the same or different from each other, are C$_1$-C$_{20}$ alkyl, cycloalkyl, alkenyl, alkynyl, aryl, arylalkyl, or alkylaryl.

In one embodiment, the compound is a compound of Formula II:

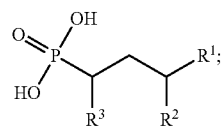

wherein
$R^1$ is CHO or CH$_2$OH;
$R^2$ is OH or =O; and
$R^3$ is OH or H.

In one embodiment, the compound is a compound of Formula III:

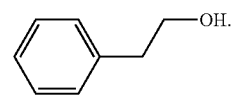

In one embodiment, the compound is a compound of Formula IV:

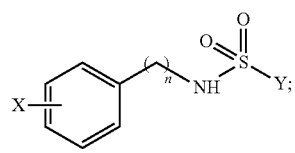

wherein
X is para-, meta- or ortho —CO$_2$H or para-, meta- or ortho- CH$_2$PO$_3$H$_2$;
Y is a saturated or unsaturated linear or branched alkyl group of 1 to 20 carbons, cycloalkyl, alkenyl, alkynyl, aryl, arylalkyl, alkylaryl, —CHR$^5$OR$^6$, —CO(O)R$^5$, —C(O)NR$^5$R$^6$, —CH$_2$C(O)R$^5$, —CH$_2$C(O)NHR$^5$, —C(O)R$^5$, —CH$_2$OR$^5$, —C(O)R$^5$, —CO(O)R$^5$, —C(O)NR$^5$R$^6$, —CH$_2$C(O)R$^5$, —CH$_2$C(O)NHR$^5$, or optionally contain halogen atoms;

$R^5$ and $R^6$ are each independently H, C$_1$-C$_{20}$ alkyl, cycloalkyl, alkenyl, alkynyl, aryl, arylalkyl, alkylaryl, or optionally contain halogen atoms; and n is 0 to 3.

In one embodiment, the compound is a compound of Formula V:

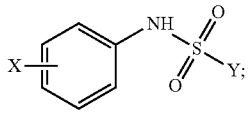

wherein
X is para-, meta- or ortho-$CO_2H$; and
Y is a saturated or unsaturated linear or branched alkyl group of 1 to 20 carbons, cycloalkyl, alkenyl, alkynyl, aryl, arylalkyl, alkylaryl, —$CHR^5OR^6$, —$CO(O)R^5$, —$C(O)NR^5R^6$, —$CH_2C(O)R^5$, —$CH_2C(O)NHR^5$, —$C(O)R^5$, —$CH_2OR^5$, —$C(O)R^5$, —$CO(O)R^5$, —$C(O)NR^5R^6$, —$CH_2C(O)R^5$, —$CH_2C(O)NHR^5$, or optionally contain halogen atoms;
$R^5$ and $R^6$ are each independently H, $C_1$-$C_{20}$ alkyl, cycloalkyl, alkenyl, alkynyl, aryl, arylalkyl, alkylaryl, or optionally contain halogen atoms.

In one embodiment, the compound is a compound of Formula VI:

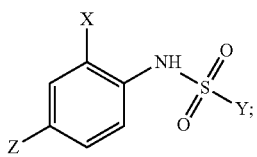

wherein
X is $CO_2H$ or para-, meta- or ortho-$PO_3H_2$;
Y is a saturated or unsaturated linear or branched alkyl group of 1 to 20 carbons, cycloalkyl, alkenyl, alkynyl, aryl, arylalkyl, alkylaryl, —$CHR^5OR^6$, —$CO(O)R^5$, —$C(O)NR^5R^6$, —$CH_2C(O)R^5$, —$CH_2C(O)NHR^5$, —$C(O)R^5$, —$CH_2OR^5$, —$C(O)R^5$, —$CO(O)R^5$, —$C(O)NR^5R^6$, —$CH_2C(O)R^5$, —$CH_2C(O)NHR^5$, or optionally contain halogen atoms;
$R^5$ and $R^6$ are each independently H, $C_1$-$C_{20}$ alkyl, cycloalkyl, alkenyl, alkynyl, aryl, arylalkyl, alkylaryl, or optionally contain halogen atoms; and
Z is H, OH, or halogen.

In one embodiment, the compound of Formula I has the structure:

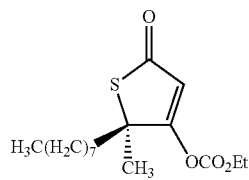

In one embodiment, the compound of Formula II is selected from the group consisting of (rac)-3,4-dihydroxybutyl-1-phosphonate, (S)-3,4-dihydroxybutyl-1-phosphonate, (rac)-3-hydroxy-4-oxobutyl-1-phosphonate, (S)-3-hydroxy-4-oxobutyl-1-phosphonate, 4-hydroxy-3-oxobutyl-1-phosphonate and 1,3,4-trihydroxybutyl-1-phosphonate. In one embodiment, the compound of Formula II is (1S,3S)-1,3,4-trihydroxybutyl-1-phosphonate or (1R,3S)-1,3,4-trihydroxybutyl-1-phosphonate.

In an embodiment of the invention, the compound is an inhibitory polynucleotide. In another embodiment, the compound is a small molecule.

According to the invention, the compound is an inhibitor of one or more enzymes selected from the group consisting of glycerol-3-phosphate acyltransferase (GPAT), acylglycerol-3-phosphate acyltransferase (AGPAT), phospholipase D (PLD) and diacylglycerol kinase (DGK).

The invention also provides a method of treating or preventing a viral infection in a mammal, comprising administering to a mammalian subject in need thereof a therapeutically effective amount of a compound or prodrug thereof, or pharmaceutically acceptable salt or ester of said compound or prodrug that inhibits a phosphatidic acid synthesis enzyme. In one embodiment, the compound that inhibits a phosphatidic acid synthesis enzyme is a small molecule. In another embodiment, the compounds is an inhibitory polynucleotide.

The invention also provides a pharmaceutical composition for treatment or prevention of a viral infection comprising a therapeutically effective amount of one or more aforementioned compounds or prodrugs thereof, or pharmaceutically acceptable salt or ester of said compound or prodrug; and (ii) a pharmaceutically acceptable carrier.

The invention also provides a pharmaceutical composition for treatment or prevention of a viral infection comprising a therapeutically effective amount of a composition comprising (i) a compound or prodrug thereof, or pharmaceutically acceptable salt or ester of said compound or prodrug that inhibits a phosphatidic acid synthesis enzyme; and (ii) a pharmaceutically acceptable carrier. In one embodiment, the phosphatidic acid synthesis enzyme is glycerol-3-P acyltransferase (GPAT), acylglycerol-3-P acyltransferase (AGPAT), phospholipase D (PLD), or diacylglycerol kinase (DGK).

In an embodiment of the invention, the viral infection is by an enveloped virus. In one particular embodiment, the virus is human cytomegalovirus (HCMV). In another embodiment, the virus is herpes simplex virus-1 (HSV-1).

DETAILED DESCRIPTION

Figure 1:
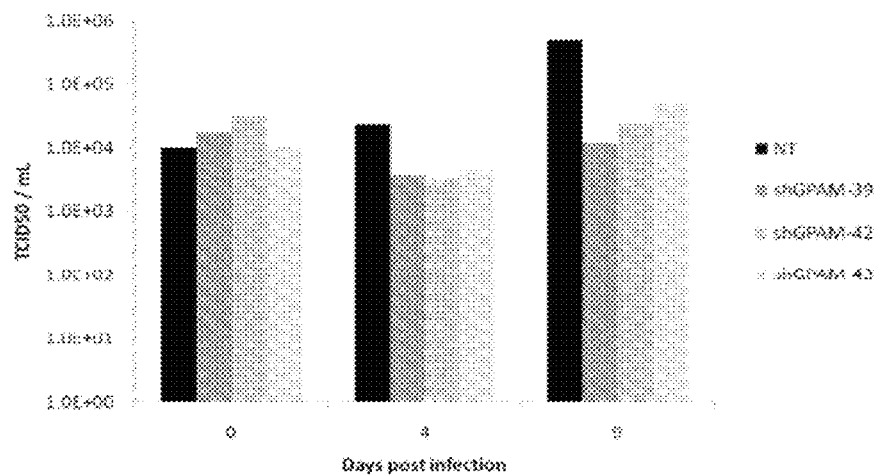
FIG. 1. Knockdown of Glycerol-3-Phosphate Acyltransferase (GPAT) Inhibits HCMV Replication. Fibroblasts were created with lentiviral transduction vectors containing either non-targeting short-hairpin RNAs or short-hairpin RNAs targeted to mitochondrial glycerol-3-phosphate acyltransferase (GPAM). Cells were infected at an MOI of 0.1 $TCID_{50}$ units/ml (A), 1.0 $TCID_{50}$ units/ml (B), or 3.0 $TCID_{50}$ units/ml (C) and harvested at 0, 4, and 9 days post infection. Harvested supernatants were then titered by $TCID_{50}$ assay on fibroblasts.
Figure 1:
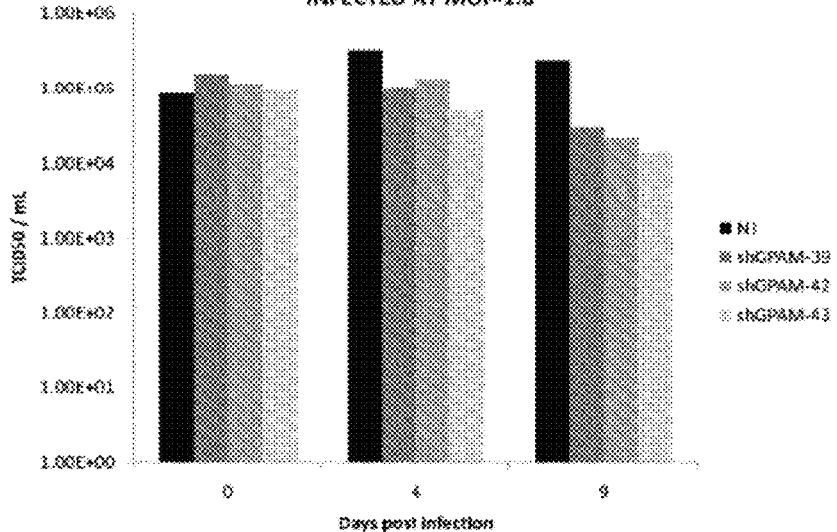
Figure 1:
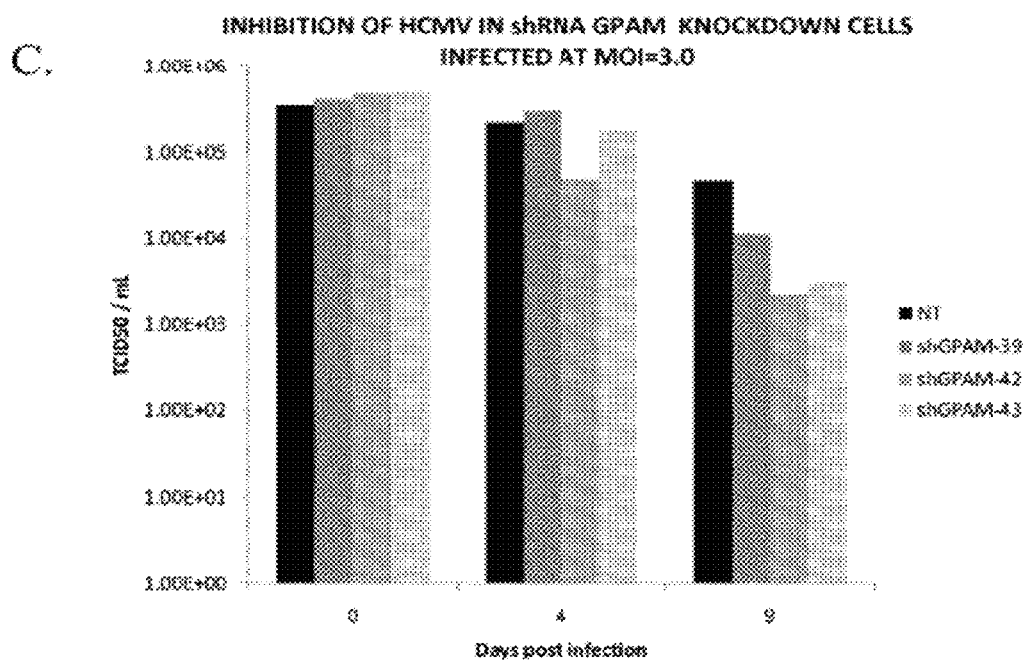

Viral replication requires energy and macromolecular precursors derived from the metabolic network of the host cell. Using an integrated approach to profiling metabolic flux, the inventors discovered alterations of certain metabolite concentrations and fluxes in response to viral infection. Details of the profiling methods are described in PCT/US2008/006959, which is incorporated by reference in its entirety. Using this approach, certain enzymes in the various metabolic pathways, especially those which serve as key "switches," have been discovered to be useful targets for intervention; i.e., as targets for redirecting the metabolic flux to disadvantage viral replication and restore normal metabolic flux profiles, thus serving as targets for antiviral therapies. Enzymes involved in initial steps in a metabolic pathway are potential enzyme targets. In addition, enzymes that catalyze "irreversible" reactions or committed steps in metabolic pathways can be advantageously used as enzyme targets for antiviral therapy. PCT/US2010/043101, which is incorporated by reference in its entirety, describes the use of mTOR kinase inhibitors as antivirals. U.S. Ser. No. 61/305,862, which is incorporated by reference in its entirety, describes inhibitors of long and very long chain fatty acid metabolism as anti-virals.

HCMV upregulates the biosynthesis of fatty acids, and inhibition of fatty acid synthesis using an antagonist of acetylCoA carboxylase or fatty acid synthase interferes with the production of both HCMV and influenza virus progeny in cultured cells (Munger et al. (2006), PLoS Pathogens 2 (12), e132; Munger et al., Nat. Biotech. (2008), 26 (10), 1179-1186). This showed that it is possible to inhibit virus replication and spread by inhibiting host cell metabolic enzymes.

The inventors have found that HCMV and other viruses are dependent on metabolic enzymes that function downstream of the synthesis of fatty acids, i.e., in the synthesis of lipids containing fatty acids; and therefore, inhibition of theses enzymes can inhibit the production of virus progeny. Further exploration of lipid-related events during viral infection led to the inventors' discovery that a variety of lipids accumulate at elevated levels after infection of cells with HCMV.

According to the invention, inhibition of GPAT and other enzymes that can produce phosphatidic acid are useful targets for inhibition of viral replication. The enzymes include glycerol-3-phosphate acyltransferase (GPAT), acylglycerol-3-phosphate acyltransferase (AGPAT), phospholipase D (PLD) and diacylglycerol kinase (DGK).

Glycerol-3-phosphate acyltransferase (GPAT) catalyzes the acylation of glycerol 3-phosphate with long-chain acyl-CoAs to form lysophosphatidic acid (LPA). Four isoforms of GPAT have been identified: two are localized to the mitochondria (mtGPAT1 and mtGPAT2) and two are localized to the endoplasmic reticulum (GPAT3 and GPAT4). Acylglycerol-3-phosphate acyltransferase (AGPAT), for which eleven isoforms have been reported, catalyzes the conversion of lysophosphatidic acid to phosphatidic acid. Phospholipase D (PLD) catalyzes the hydrolysis of phosphatidylcholine to form phosphatidic acid. Two isoforms of PLD have been identified by cDNA cloning. Diacylglycerol kinase (DGK) catalyzes the conversion of diacylglycerol to phosphatidic acid, utilizing ATP as a phosphate source. Ten isoforms have been identified and categorized into subfamilies by structural motifs and expression patterns. For the most part, each isoform is expressed in numerous tissues, and several may be expressed in the same cell.

The compounds of the invention inhibit viral replication by targeting cellular enzymes, rather than virus-coded products. Existing antivirals target virus-coded products, and as a result, mutant viruses arise rapidly that are resistant to the drugs. Resistant viruses are unlikely to arise rapidly when a cellular target is inhibited using the compounds of the invention. Further, as particular cellular enzymes support replication of several different viruses, inhibitors of those enzymes are likely to be broad-spectrum antivirals.

The subsections below describe in more detail the antiviral compounds and target enzymes of the invention, screening assays for identifying and characterizing new antiviral compounds, and methods for their use as antiviral therapeutics to treat and prevent viral infections. The compounds of the invention include inhibitors of one or more enzymes selected from the group consisting of GPAT, AGPAT, PLD and DGK. These compounds include, but are not limited to the following compounds, relative, analogs, or derivatives: FAS 115 and related compounds, (S)-3,4-dihydroxybutyl-1-phosphonate, (rac)-3,4-dihydroxybutyl-1-phosphonate, (S)-3,4-dihydroxybutyl-1-phosphonate, (rac)-3-hydroxy-4-oxobutyl-1-phosphonate, 4-hydroxy-3-oxobutyl-1-phosphonate, 1,3,4-trihydroxybutyl-1-phosphonate, (1S,3S)-1,3,4-trihydroxybutyl-1-phosphonate and (1R,3S)-1,3,4-trihydroxybutyl-1-phosphonate; phenethyl alcohol; and substituted benzoic and phosphonic acids. Compounds of the invention further include inhibitory nucleic acids.

Preferably, the compounds are selective inhibitors. For example, preferred GPAT inhibitors show >2-fold, >5-fold, >10-fold, >20-fold, >50-fold or >100-fold selectivity for inhibition of GPAT as compared to other cellular enzymes, particularly cellular enzymes involved in fatty acid metabolism, as measured by comparing, for example, the $IC_{50}$ values.

1. Target Enzymes

As indicated below, in virus infected cells, the most obvious changes in glycerol phospholipids were absolute increases in saturated and monounsaturated phosphatidic acid (PA) species. Accordingly, the invention provides methods of treating viral infection using inhibitors or other modulators of these enzymes involved in phosphatidic acid production. These enzymes include glycerol-3-phosphate acyltransferase (GPAT), acylglycerol-3-phosphate acyltransferase (AGPAT), phospholipase D (PLD) and diacylglycerol kinase (DGK). Glycerol-3-phosphate acyltransferase (GPAT) catalyzes the synthesis of lysophosphatidic acid (LPA) from glycerol 3-phosphate and long-chain acyl-CoA. Acylglycerol-3-phosphate acyltransferase (AGPAT) converts lysophosphatidic acid to phosphatidic acid. Phospholipase D (PLD) catalyzes the hydrolysis of phosphatidylcholine to form phosphatidic acid. Diacylglycerol kinase (DGK) catalyzes the conversion of diacylglycerol to phosphatidic acid. According to the invention, one or more of such phosphatidic acid synthesis enzymes is targeted.

In one embodiment, GPAT can be targeted with a small molecule inhibitor, including but not limited to FAS 115 or other compound described herein, or with an inhibitory nucleic acid that reduces or blocks expression of GPAT. Another way to target GPAT is with both a small molecule inhibitor and an inhibitory nucleic acid. Further, combinations of phosphatidic acid synthesis may be targeted. In one non-limiting example, a GPAT inhibitor is administered in combination with an AGPAT inhibitor, reducing or blocking both conversion of glycerol 3-phosphate to lysophosphatidic acid and conversion of lysophosphatidic acid to phosphatidic acid. In another such example, a GPAT inhibitor is administered in combination with a phospholipase D inhibitor, thus reducing or blocking formation of phosphatidic acid from glycerol 3-phosphate and from phosphatidylcholine. In yet another such example, a GPAT inhibitor is administered in combination with a diacylglycerol kinase inhibitor, thus reducing or blocking formation of phosphatidic acid from glycerol 3-phosphate and from diacylglycerol. Other combinations include, but are not limited to, an AGPAT inhibitor with a PLD inhibitor, an AGPAT inhibitor with a DGK inhibitor, and a PLD inhibitor with a DGK inhibitor.

Lipid-related processes are essential to viral growth, replication and/or other elements of infection. Consequently, it is likely that multiple cellular enzymes that function in lipid metabolism are needed for successful infection, and it is possible that simultaneous inhibition of multiple enzymes (e.g., two or more different enzymes) will produce a synergistic inhibition of infection or allow the use of lower doses of each compound to achieve a desirable therapeutic effect. Accordingly, the present invention provides for administering to the mammal two or more compounds described herein, wherein each compound targets one or more different enzymes described herein. In some embodiments, such combination therapy is sequential; in other embodiments, it is simultaneous. In some embodiments, the two or more agents are formulated together to create a composition comprising two or more compounds for the prevention and/or treatment of viral infection via modulation of host cell lipid and/or cholesterol metabolism. In some embodiments, the dose of one of the compounds is substantially less, e.g., 1.5, 2, 3, 5, 7, or 10-fold less, than required when used independently for the prevention and/or treatment of viral infection. In some embodiments, the dose of both agents is reduced by 1.5, 2, 3, 5, 7, or 10-fold or more.

According to the invention, an inhibitor of phosphatidic acid synthesis can be combined with an inhibitor of fatty acid biosynthesis. For example, inhibition of fatty acid synthesis by an antagonist of acetyl CoA carboxylase (ACC) interferes with the production of human cytomegalovirus and influenza virus. Thus, an inhibitor of phosphatidic acid synthesis can be used in combination with an ACC antagonist. A useful ACC antagonist is 5-(tetradecyloxy)-2-furoic acid (TOFA). TOFA and related compounds are disclosed in PCT/US2008/006959 and Parker et al., 1977, J. Med. Chem. 20:781-91, which are incorporated by reference in their entireties. Other useful ACC antagonists include, without limitation, CP-610431 and CP-640186 (Pfizer; see Harwood et al., 2003, J Biol Chem. 278:37099). In some embodiments, compounds that target and inhibit ACC include, but are not limited to, pseudopeptide pyrrolidine dione antibiotics, e.g., moiramide B and synthetic analogs thereof, and andrimid and synthetic analogs thereof; and pyrrolidinedione derivatives. See Freiberg et al., J. Biol. Chem. 279:26066-26073, 2004; Freiberg et al., Antimicrob. Agents Chemother. 49:749-759, 2005; and Pohlmann et al., Bioorg. Med. Chem. Lett. 15:1189-1192, 2005, which are incorporated herein in their entirety. In some embodiments, a Compound is a pyrrolidinedione derivative. Non-limiting examples of pyrrolidinedione derivatives are disclosed in Pohlmann et al., Bioorg. Med. Chem. Lett. 2005 15:1189-1192.

In another embodiment, an inhibitor of phosphatidic acid synthesis is used in combination with an inhibitor of a long or very long chain fatty acid synthesis enzyme or an elongase. Non-limiting examples of such enzymes are acyl-CoA synthetase long chain family member 1 (ACSL1), elongation of very long chain fatty acids 2, 3 and 6 (ELOVL2, ELOVL3 and ELOVL6), and solute carrier family 27 (fatty acid transporter) member 3 (SLC27A3), all of which are enzymes involved in synthesis of long and very long chain acyl-CoA species. Long-chain acyl-CoA synthetases (ACSLs) (E.C.6.2.1.3) catalyze esterification of long-chain fatty acids, mediating the partitioning of fatty acids in mammalian cells. ACSL isoforms (ACSL1, ACSL3, ACSL4, ACSL5, and ACSL6) generate bioactive fatty acyl-CoAs from CoA, ATP, and long-chain (C12-C20) fatty acids. Knockdown of any of these enzymes inhibits the production of infectious HCMV.

Triacsin C inhibits long chain acyl-CoA synthetases (ACSLs). Triacsin C is a member of a family of related compounds (Triacsins A-D) isolated from the culture filtrate of *Streptomyces* sp. SK-1894 (Omura et al., J Antibiot 39, 1211-8, 1986; Tomoda et al., Biochim Biophys Acta, 921, 595-8, 1987), all of which consist of 11-carbon alkenyl chains with a common triazenol moiety at their termini. Triacsin C and other inhibitors of the aforementioned targets are disclosed in U.S. Ser. No. 61/305,862, and are otherwise known in the art.

One example of an ELOVL6 inhibitor is

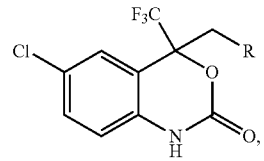

wherein R is selected from

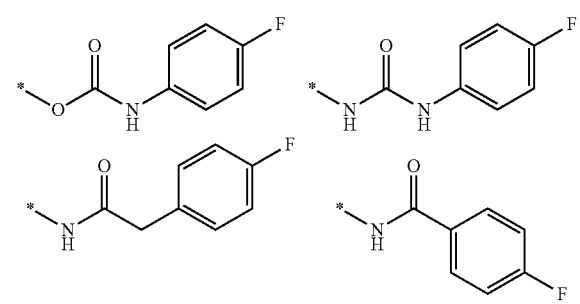

In another embodiment, the ELOVL6 inhibitor is

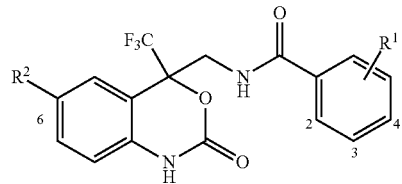

wherein R¹ is substituted at position 2, 3, or 4 with F, or Me, or R¹ is substituted at position 4 with MeO, or CF₃. R² is Cl, H, Ph, 4-isoxazol, 4-pyrazol, 3-pyrazol, 1-pyrazol, 5-(1,2,4-triazol), 1-(1,2,4-triazol), 2-imidazol, 1-(2-pyrrolidone), or 3-(1,3-oxazolidin-2-one). In one embodiment the compound is

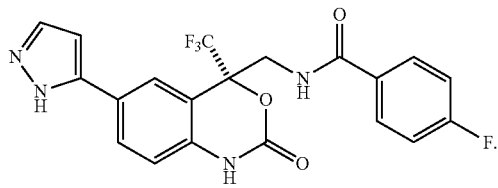 [SMILES: O=C1Nc2ccc(-c3ccn[nH]3)cc2[C@](CNC(=O)c2ccc(F)cc2)(C(F)(F)F)O1]

(See, Mizutani et al., 2009, J. Med. Chem. 52:7289-7300).

Another example of an ELOVL6 inhibitor is

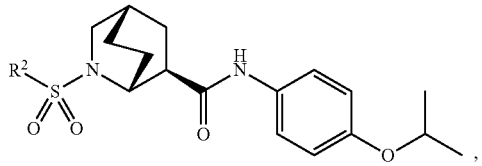

wherein R² is selected from butyl, propyl, phenyl, pyridyl, and imidazole. (See, Sasaki et al., 2009, Biorg. Med. Chem. 17:5639-47.)

Yet another example of an ELOVL6 inhibitor is

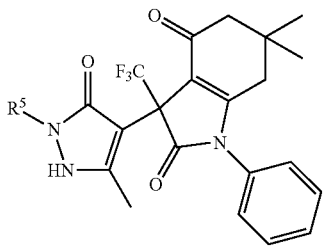

wherein R⁵ is a substituted phenyl ring, including, but not limited to

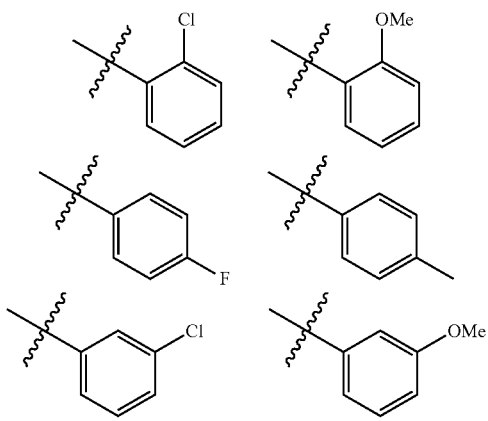

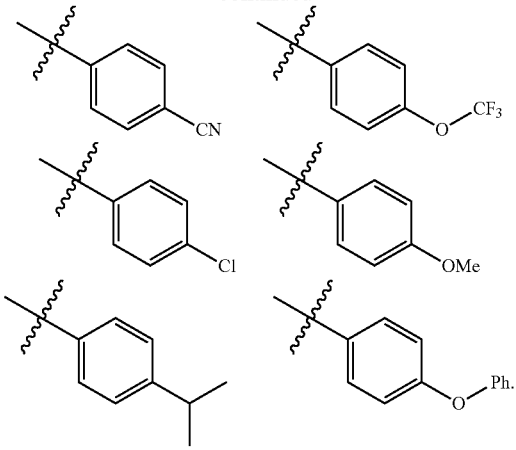

(See Takahashi et al., 2009, J. Med. Chem. 52:3142-5.)

In another embodiment, the triacsin compound or relative or analog is combined with an inhibitor of HMG-CoA reductase. Exemplary HMG-CoA reductase inhibitors are well known in the art and include, but are not limited to, mevastatin and related molecules (e.g., see U.S. Pat. No. 3,983,140); lovastatin (mevinolin) and related molecules (e.g., see U.S. Pat. No. 4,231,938); pravastatin and related molecules (e.g., see U.S. Pat. No. 4,346,227); simvastatin and related molecules (e.g., see U.S. Pat. Nos. 4,448,784 and 4,450,171); fluvastatin (e.g., see U.S. Pat. No. 5,354,772); cerivastatin (e.g., see U.S. Pat. Nos. 5,006,530 and 5,177,080); atorvastatin (e.g., see U.S. Pat. Nos. 4,681,893, 5,273,995, 5,385,929 and 5,686,104); itavastatin (e.g., see U.S. Pat. No. 5,011,930); Shionogi-Astra/Zeneca visastatin (ZD-4522) (e.g., see U.S. Pat. No. 5,260,440), related statin compounds (e.g., see U.S. Pat. No. 5,753,675); pyrazole analogs of mevalonolactone derivatives (e.g., see U.S. Pat. No. 4,613,610); indene analogs of mevalonolactone derivatives (e.g., see International Patent Application Publication No. WO 1986/03488); 642-(substituted-pyrrol-1-yl)-alkyl)pyran-2-ones and derivatives thereof (e.g., see U.S. Pat. No. 4,647,576); Searle's SC-45355 (a 3-substituted pentanedioic acid derivative) dichloroacetate, imidazole analogs of mevalonolactone (e.g., see International Patent Application No. WO 1986/07054); 3-carboxy-2-hydroxy-propane-phosphonic acid derivatives; naphthyl analogs of mevalonolactone (e.g., see U.S. Pat. No. 4,686,237); octahydronaphthalenes (e.g., see U.S. Pat. No. 4,499,289); keto analogs of mevinolin (lovastatin); phosphinic acid compounds (e.g., see GB 2205837); and quinoline and pyridine derivatives (e.g., see U.S. Pat. Nos. 5,506,219 and 5,691,322). Each of the references above is incorporated by reference herein in its entirety. The structures of such exemplary HMG-CoA reductase inhibitors are well known in the art.

In yet another embodiment, an inhibitor of phosphatidic acid synthesis is used in combination with an mTOR inhibitor. Elevated phosphatidic acid levels stimulate mTORC1 and mTORC2 formation and cause partial resistance to rapamycin. Consequently, inhibitors of phosphatidic acid synthesis enzymes would increase sensitivity to mTOR inhibitors. In one embodiment, the mTOR inhibitor used in combination with the inhibitor of phosphatidic acid synthesis is a specific inhibitor of mTOR. In other embodiments the mTOR inhibitor is less specific with significant activity against other protein kinases such as XL765, PI-103, PF-4691502, LY294002, and LOR-220. In other embodiments, the inhibitor of mTOR inhibits a rapamycin-resistant function of mTOR, a rapamycin-sensitive sensitive function of mTOR, or both.

mTOR inhibitors that can be used include rapamycin and its analogs ("rapalogs") such as: norrapamycin, everolimus, temsirolimus (CCI-779), ridaforolimus (AP23573), zotarolimus, deoxorapamycin, desmethylrapamycins, desmethoxyrapamycins, AP22594,28-epi-rapamycin, 24,30-tetrahydro-rapamycin, ridaforolimus (AP23573), trans-3-azabicyclo[3.1.0]hexane-2-carboxylic acid rapamycin, ABT-578, SDZ RAD, AP20840, AP23464, AP23675, AP23841, AP24170, TAFA93,40-O-(2-hydroxyethyl)-rapamycin, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxy-methyl)-2-methylpropanoate]-rapamycin (CC1779), 40-epi-(tetrazolyl)-rapamycin (ABT578), TAFA-93, biolimus-7, biolimus-9, biolimus A9 and combinations. mTOR kinase inhibitors that can be used include torin1 and its analogs. WO2010/044885, which is incorporated by reference in its entirety, describes such small molecule modulators of mTOR. The compound, Ku-0063794, is a selective inhibitor of mTOR with an $IC_{50}$ of about 10 nM (Garcia-Martinez et al. *Biochem. J.* 421:29-42, which is incorporated by reference). WO2010/006072, which is incorporated by reference in its entirety describes PP30 and PP242 and their analogs. In addition to the compounds disclosed above, selective mTOR inhibitors that can be used in the present invention include KU-BMCL-200908069-1; KU-BMCL-200908069-5 ($IC_{50}$ 21 nmol; >500-fold selective versus PI3Ks); WAY-600 ($IC_{50}$ 9 nmol; >100-fold selective versus $PI3K\alpha$ and >500 selective versus $PI3K\gamma$); WYE-687 ($IC_{50}$ 7 nmol; >100-fold selective versus $PI3K\alpha$ and >500 selective versus $PI3K\gamma$); WYE354 ($IC_{50}$ 5 nmol; >100-fold selective versus $PI3K\alpha$ and >500 selective versus $PI3K\gamma$); Wyeth-BMCL-200910075-9b ($IC_{50}$ 0.7 nmol; >1.000-fold selective versus PI3K); Wyeth-BMCL-200910096-27 ($IC_{50}$ 0.6 nmol; >200-fold selective versus $PI3K\alpha$); INK128 (Intellikine, Inc.) ($IC_{50}$ 1 nmol; >100-fold selective versus PI3Ks); XL388 (Exelixis) ($IC_{50}$ 9.8 nmol against mTORC1 and 166 nM against mTORC2; >100-fold selective versus a panel of 140 protein kinases ($IC_{50}$>3 µM)); AZD8055 (Astra Zeneca) ($IC_{50}$ 0.13 nmol; >10.000-fold selective versus p100α); and OSI-027 (OSI pharmaceuticals). Another ATP-competitive specific mTOR inhibitor is WYE-125132 ($IC_{50}$ 0.19 nmol; >5.000-fold selective versus PI3Ks). Other mTOR inhibitors that can be used in the present invention include those disclosed in WO2006/090167, WO2006/090169, WO2007/060404, WO2007/080382, WO2007/060404, and WO2008/023161.

2. GPAT Inhibitors

In one embodiment, the present invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of Formula I:

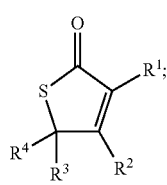

(I)

wherein $R^1$ and $R^2$ are each independently —H, —OH, —$OR^5$, —$OCH_2C(O)R^5$, —$OCH_2C(O)NHR^5$, —$OC(O)R^5$, —$OC(O)OR^5$, —$OC(O)NHNH$—$R^5$, —$OC(O)NR^5R^6$, $C_1$-$C_{20}$ alkyl, cycloalkyl, alkenyl, alkynyl, aryl, arylalkyl, alkylaryl, —$CHR^5OR^6$, —$CO(O)R^5$, —$C(O)NR^5R^6$, —$CH_2C(O)R^5$, —$CH_2C(O)NHR^5$, —$C(O)R^5$, —$CH_2OR^5$, —$C(O)R^5$, —$CO(O)R^5$, —$C(O)NR^5R^6$, —$CH_2C(O)R^5$, or —$CH_2C(O)NHR^5$, $R^5$ and $R^6$ are each independently H, $C_1$-$C_{20}$ alkyl, cycloalkyl, alkenyl, alkynyl, aryl, arylalkyl, alkylaryl, or optionally contain halogen atoms;

$R^3$ and $R^4$, the same or different from each other, are $C_1$-$C_{20}$ alkyl, cycloalkyl, alkenyl, alkynyl, aryl, arylalkyl, or alkylaryl.

In one embodiment, the compound of Formula I is

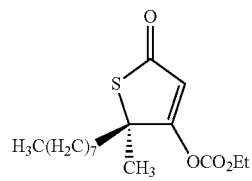

also known as FAS 115. FAS 115 inhibits GPAT (FASgen LLC, UMB Research Park, Building One, 800 W. Baltimore Street, Suite 150, Baltimore, Md. 21201). WO 2004/005277, which is incorporated by reference in its entirety, describes the synthesis of FAS 115, a 5,5-disubstituted thiotetronic ethyl carbonate (a thiophene-2-one).

In one embodiment, the present invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of Formula II:

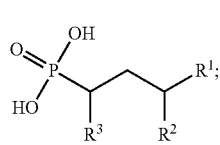

(II)

wherein $R^1$ is CHO or $CH_2OH$;

$R^2$ is OH or =O; and $R^3$ is OH or H.

Particular compounds of Formula II are (rac)-3,4-dihydroxybutyl-1-phosphonate, (S)-3,4-dihydroxybutyl-1-phosphonate, (rac)-3-hydroxy-4-oxobutyl-1-phosphonate, (S)-3-hydroxy-4-oxobutyl-1-phosphonate, 4-hydroxy-3-oxobutyl-1-phosphonate and 1,3,4-trihydroxybutyl-1-phosphonate. In one embodiment, the 1,3,4-trihydroxybutyl-1-phosphonate is (1S,3S)-1,3,4-trihydroxybutyl-1-phosphonate or (1R,3S)-1,3,4-trihydroxybutyl-1-phosphonate.

For treating or preventing viral infection in a mammal, the invention also provides a compound of Formula III:

$$\text{(III)}$$

Stein et al. (Biochimica et Biophysica Acta, 1123 (1992), 249-256), which is incorporated in its entirety, describes inhibition of GPAT using glycerol-3-phosphate analogs and phenethyl alcohol.

In one embodiment, the present invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of Formula IV:

$$\text{(IV)}$$

wherein

X is para-, meta- or ortho —$CO_2H$ or para-, meta- or ortho-$CH_2PO_3H_2$;

Y is a saturated or unsaturated linear or branched alkyl group of 1 to 20 carbons, cycloalkyl, alkenyl, alkynyl, aryl, arylalkyl, alkylaryl, —$CHR^5OR^6$, —$CO(O)R^5$, —$C(O)NR^5R^6$, —$CH_2C(O)R^5$, —$CH_2C(O)NHR^5$, —$C(O)R^5$, —$C(O)R^5$, —$CO(O)R^5$, —$C(O)NR^5R^6$, —$CH_2C(O)R^5$, —$CH_2C(O)NHR^5$, or optionally contain halogen atoms;

$R^5$ and $R^6$ are each independently H, $C_1$-$C_{20}$ alkyl, cycloalkyl, alkenyl, alkynyl, aryl, arylalkyl, alkylaryl, or optionally contain halogen atoms; and n is 0 or 1.

In one embodiment, the present invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of Formula V:

$$\text{(V)}$$

wherein

X is para-, meta- or ortho-$CO_2H$; and

Y is a saturated or unsaturated linear or branched alkyl group of 1 to 20 carbons, cycloalkyl, alkenyl, alkynyl, aryl, arylalkyl, alkylaryl, —$CHR^5OR^6$, —$CO(O)R^5$, —$C(O)NR^5R^6$, —$CH_2C(O)R^5$, —$CH_2C(O)NHR^5$, —$C(O)R^5$, —$CH_2OR^5$, —$C(O)R^5$, —$CO(O)R^5$, —$C(O)NR^5R^6$, —$CH_2C(O)R^5$, —$CH_2C(O)NHR^5$, or optionally contain halogen atoms;

$R^5$ and $R^6$ are each independently H, $C_1$-$C_{20}$ alkyl, cycloalkyl, alkenyl, alkynyl, aryl, arylalkyl, alkylaryl, or optionally contain halogen atoms.

In one embodiment, the present invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of Formula VI:

$$\text{(VI)}$$

wherein

X is $CO_2H$ or para-, meta- or ortho-$PO_3H_2$;

Y is a saturated or unsaturated linear or branched alkyl group of 1 to 20 carbons, cycloalkyl, alkenyl, alkynyl, aryl, arylalkyl, alkylaryl, —$CHR^5OR^6$, —$CO(O)R^5$, —$C(O)NR^5R^6$, —$CH_2C(O)R^5$, —$CH_2C(O)NHR^5$, —$C(O)R^5$, —$CH_2OR^5$, —$C(O)R^5$, —$CO(O)R^5$, —$C(O)NR^5R^6$, —$CH_2C(O)R^5$, —$CH_2C(O)NHR^5$, or optionally contain halogen atoms;

$R^5$ and $R^6$ are each independently H, $C_1$-$C_{20}$ alkyl, cycloalkyl, alkenyl, alkynyl, aryl, arylalkyl, alkylaryl, or optionally contain halogen atoms; and Z is H, OH, or halogen.

Wydysh et al. (J. Med. Chem. (2009), 52, 3317-3327), which is incorporated in its entirety, describes the design and synthesis of such small molecule GPAT inhibitors, including substituted benzoic and phosphonic acids, for use in treatment of obesity and associated diseases.

In one embodiment, the compound is an inhibitor of one or more enzymes selected from the group consisting of glycerol-3-phosphate acyltransferase (GPAT), acylglycerol-3-phosphate acyltransferase (AGPAT), phospholipase D (PLD) and diacylglycerol kinase (DGK).

2.1 Small Molecule Inhibitors

Compounds of the invention include small molecules. As used herein, the terms "chemical agent" and "small molecule" are used interchangeably, and both terms refer to substances that have a molecular weight up to about 4000 atomic mass units (Daltons), preferably up to about 2000 Daltons, and more preferably up to about 1000 Daltons. Unless otherwise stated herein, the term "small molecule" as used herein refers exclusively to chemical agents, and does not refer to biological agents. As used herein, "biological agents" are molecules which include proteins, polypeptides, and nucleic acids, and have molecular weights equal to or greater than about 2000 atomic mass units (Daltons). Compounds of the invention include salts, esters, and other pharmaceutically acceptable forms of such compounds.

In certain embodiments, compounds of the invention may exist in several tautomeric forms. Accordingly, the chemical structures depicted herein encompass all possible tautomeric forms of the illustrated compounds. Compounds of the invention may exist in various hydrated forms.

Definitions of the more commonly recited chemical groups are set forth below. Certain variables in classes of compounds disclosed herein recite other chemical groups. Chemical groups recited herein, but not specifically defined, have their ordinary meaning as would be known by a chemist skilled in the art.

The terms "halogen" and "halo" mean fluorine, chlorine, bromine and iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like. An aryl group can be substituted or unsubstituted.

A "cycloalkyl" group is a saturated or unsaturated non-aromatic carbocyclic ring. Representative cycloalkyl groups include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. A cycloalkyl group can be substituted or unsubstituted.

A "substituted" group may be substituted with any suitable substituent or substituents. Illustrative examples of substituents include those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art; see for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

As used herein and unless otherwise indicated, the term "hydrate" means a compound, or a salt thereof, that further includes a stoichiometric or non-stoichiometric amount of water bound by non-covalent intermolecular forces.

As used herein and unless otherwise indicated, the term "solvate" means a compound, or a salt thereof, that further includes a stoichiometric or non-stoichiometric amount of a solvent bound by non-covalent intermolecular forces.

As used herein and unless otherwise indicated, the term "prodrug" means a compound derivative that can hydrolyze, oxidize, or otherwise react under biological conditions (in vitro or in vivo) to provide a compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

As used herein and unless otherwise indicated, the term "stereoisomer" or "stereomerically pure" means one stereoisomer of a compound, in the context of an organic or inorganic molecule, that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments disclosed herein, including mixtures thereof.

Various compounds contain one or more chiral centers, and can exist as racemic mixtures of enantiomers, mixtures of diastereomers or enantiomerically or optically pure compounds. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should also be noted that compounds, in the context of organic and inorganic molecules, can include E and Z isomers, or a mixture thereof, and cis and trans isomers or a mixture thereof. In certain embodiments, compounds are isolated as either the E or Z isomer. In other embodiments, compounds are a mixture of the E and Z isomers.

According to the invention, GPAT inhibitors, or related compounds or analogs or prodrugs thereof, are used for treating or preventing infection by a virus that depends on maintaining GPAT function for replication and or spread. In one embodiment, GPAT inhibitors, or related compounds or analogs thereof, [includes unrelated compounds?] are used for treating or preventing infection by a herpesvirus. Herpesvirus (Herpesviridae) is a family of viruses comprising a double-stranded DNA genome. For example, as exemplified herein, nanomolar concentrations of GPAT inhibitors inhibit the replication of HCMV, a β-herpesvirus, and herpes simplex virus-1 (HSV-1), an α-herpesvirus. Further, GPAT inhibitors exhibits broad spectrum anti-viral activity against enveloped viruses. Accordingly, in one embodiment of the invention, GPAT inhibitors are used for treating or preventing infection by an enveloped virus.

As used herein, the term "effective amount" in the context of administering a therapy to a subject refers to the amount of a therapy which is sufficient to achieve one, two, three, four, or more of the following effects: (i) reduce or ameliorate the severity of a viral infection or a symptom associated therewith; (ii) reduce the duration of a viral infection or a symptom associated therewith; (iii) prevent the progression of a viral infection or a symptom associated therewith; (iv) cause regression of a viral infection or a symptom associated therewith; (v) prevent the development or onset of a viral infection or a symptom associated therewith; (vi) prevent the recurrence of a viral infection or a symptom associated therewith; (vii) reduce or prevent the spread of a virus from one cell to another cell, or one tissue to another tissue; (ix) prevent or reduce the spread of a virus from one subject to another subject; (x) reduce organ failure associated with a viral infection; (xi) reduce hospitalization of a subject; (xii) reduce hospitalization length; (xiii) increase the survival of a subject with a viral infection; (xiv) eliminate a virus infection; and/or (xv) enhance or improve the prophylactic or therapeutic effect(s) of another therapy.

As used herein, the term "effective amount" in the context of a compound for use in cell culture-related products refers to an amount of a compound which is sufficient to reduce the viral titer in cell culture or prevent the replication of a virus in cell culture.

A preferred dose of a GPAT inhibitor used to treat or prevent viral infections in mammals is <100 mg/kg, <50 mg/kg, <20 mg/kg, <10 mg/kg, <5 mg/kg, <2 mg/kg, <1 mg/kg, <0.5 mg/kg, <0.2 mg/kg, <0.1 mg/kg, <0.05 mg/kg, <0.02 mg/kg, or <0.01 mg/kg. A preferred dose of a GPAT inhibitor used to treat or prevent viral infections in mammals results in total serum concentrations of <100 µM, <50 µM, <20 µM, <10 µM, <5 µM, <1 µM, <500 nM, or <250 nM.

The present invention also provides for the use of a GPAT inhibitor in cell culture-related products in which it is desirable to have antiviral activity. In one embodiment, a GPAT inhibitor is added to cell culture media. A GPAT inhibitor used in cell culture media includes compounds that may otherwise be found too toxic for treatment of a subject.

2.2 RNAi Molecules

According to the invention, RNA interference (RNAi) is used to reduce expression of a target protein in a cell in order to reduce viral replication and/or production of infectious virus. In certain embodiments, a compound is an RNA interference (RNAi) molecule that can decrease the expression level of a target protein. RNAi molecules include, but are not limited to, small-interfering RNA (siRNA), short hairpin RNA (shRNA), microRNA (miRNA), and any molecule capable of mediating sequence-specific RNAi.

RNA interference (RNAi) is a sequence specific post-transcriptional gene silencing mechanism triggered by double-stranded RNA (dsRNA) that have homologous sequences to the target mRNA. RNAi is also called post-transcriptional gene silencing or PTGS. See, e.g., Couzin, 2002, Science 298:2296-2297; McManus et al., 2002, Nat. Rev. Genet. 3, 737-747; Hannon, G. J., 2002, Nature 418, 244-251; Paddison et al., 2002, Cancer Cell 2, 17-23. dsRNA is recognized and targeted for cleavage by an RNaseIII-type enzyme termed Dicer. The Dicer enzyme "dices" the RNA into short duplexes of about 21 to 23 nucleotides, termed siRNAs or short-interfering RNAs (siRNAs), composed of 19 nucleotides of perfectly paired ribonucleotides with about two three unpaired nucleotides on the 3' end of each strand. These short duplexes associate with a multiprotein complex termed RISC, and direct this complex to mRNA transcripts with sequence similarity to the siRNA. As a result, nucleases present in the RNA-induced silencing complex (RISC) cleave and degrade the target mRNA transcript, thereby abolishing expression of the gene product.

Numerous reports in the literature purport the specificity of siRNAs, suggesting a requirement for near-perfect identity with the siRNA sequence (Elbashir et al., 2001. EMBO J. 20:6877-6888; Tuschl et al., 1999, Genes Dev. 13:3191-3197; Hutvagner et al., Sciencexpress 297:2056-2060). One report suggests that perfect sequence complementarity is required for siRNA-targeted transcript cleavage, while partial complementarity will lead to translational repression without transcript degradation, in the manner of microRNAs (Hutvagner et al., Sciencexpress 297:2056-2060).

miRNAs are regulatory RNAs expressed from the genome, and are processed from precursor stem-loop (short hairpin) structures (approximately 80 nucleotide in length) to produce single-stranded nucleic acids (approximately 22 nucleotide in length) that bind (or hybridizes) to complementary sequences in the 3' UTR of the target mRNA (Lee et al., 1993, Cell 75:843-854; Reinhart et al., 2000, Nature 403:901-906; Lee et al., 2001, Science 294:862-864; Lau et al., 2001, Science 294:858-862; Hutvagner et al., 2001, Science 293:834-838). miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728).

Short hairpin RNA (shRNA) is a single-stranded RNA molecule comprising at least two complementary portions hybridized or capable of hybridizing to form a double-stranded (duplex) structure sufficiently long to mediate RNAi upon processing into double-stranded RNA with overhangs, e.g., siRNAs and miRNAs. shRNA also contains at least one noncomplementary portion that forms a loop structure upon hybridization of the complementary portions to form the double-stranded structure. shRNAs serve as precursors of miRNAs and siRNAs.

Usually, sequence encoding an shRNA is cloned into a vector and the vector is introduced into a cell and transcribed by the cell's transcription machinery (Chen et al., 2003, *Biochem Biophys Res Commun* 311:398-404). The shRNAs can then be transcribed, for example, by RNA polymerase III (Pol III) in response to a Pol III-type promoter in the vector (Yuan et al., 2006, *Mol Biol Rep* 33:33-41 and Scherer et al., 2004, *Mol Ther* 10:597-603). The expressed shRNAs are then exported into the cytoplasm where they are processed by proteins such as Dicer into siRNAs, which then trigger RNAi (Amarzguioui et al., 2005, *FEBS Letter* 579:5974-5981). It has been reported that purines are required at the 5' end of a newly initiated RNA for optimal RNA polymerase III transcription. More detailed discussion can be found in Zecherle et al., 1996, *Mol. Cell. Biol.* 16:5801-5810; Fruscoloni et al., 1995, *Nucleic Acids Res,* 23:2914-2918; and Mattaj et al., 1988, *Cell,* 55:435-442. The shRNAs core sequences can be expressed stably in cells, allowing long-term gene silencing in cells both in vitro and in vivo, e.g., in animals (see, McCaffrey et al., 2002, *Nature* 418:38-39; Xia et al., 2002, *Nat. Biotech.* 20:1006-1010; Lewis et al., 2002, *Nat. Genetics* 32:107-108; Rubinson et al., 2003, *Nat. Genetics* 33:401-406; and Tiscornia et al., 2003, *Proc. Natl. Acad. Sci. USA* 100:1844-1848).

Martinez et al. reported that RNA interference can be used to selectively target oncogenic mutations (Martinez et al., 2002, Proc. Natl. Acad. Sci. USA 99:14849-14854). In this report, an siRNA that targets the region of the R248W mutant of p53 containing the point mutation was shown to silence the expression of the mutant p53 but not the wild-type p53.

Wilda et al. reported that an siRNA targeting the M-BCR/ABL fusion mRNA can be used to deplete the M-BCR/ABL mRNA and the M-BCR/ABL oncoprotein in leukemic cells (Wilda et al., 2002, Oncogene 21:5716-5724).

U.S. Pat. No. 6,506,559 discloses a RNA interference process for inhibiting expression of a target gene in a cell. The process comprises introducing partially or fully doubled-stranded RNA having a sequence in the duplex region that is identical to a sequence in the target gene into the cell or into the extracellular environment.

U.S. Patent Application Publication No. US 2002/0086356 discloses RNA interference in a *Drosophila* in vitro system using RNA segments 21-23 nucleotides (nt) in length. The patent application publication teaches that when these 21-23 nt fragments are purified and added back to *Drosophila* extracts, they mediate sequence-specific RNA interference in the absence of long dsRNA. The patent application publication also teaches that chemically synthesized oligonucleotides of the same or similar nature can also be used to target specific mRNAs for degradation in mammalian cells.

International Patent Application Publication No. WO 2002/44321 discloses that double-stranded RNA (dsRNA) 19-23 nt in length induces sequence-specific post-transcriptional gene silencing in a *Drosophila* in vitro system. The PCT publication teaches that short interfering RNAs (siRNAs) generated by an RNase III-like processing reaction from long dsRNA or chemically synthesized siRNA duplexes with overhanging 3' ends mediate efficient target RNA cleavage in the lysate, and the cleavage site is located near the center of the region spanned by the guiding siRNA.

U.S. Patent Application Publication No. US 2002/016216 discloses a method for attenuating expression of a target gene in cultured cells by introducing double stranded RNA (dsRNA) that comprises a nucleotide sequence that hybridizes under stringent conditions to a nucleotide sequence of the target gene into the cells in an amount sufficient to attenuate expression of the target gene.

International Patent Application Publication No. WO 2003/006477 discloses engineered RNA precursors that when expressed in a cell are processed by the cell to produce targeted small interfering RNAs (siRNAs) that selectively silence targeted genes (by cleaving specific mRNAs) using the cell's own RNA interference (RNAi) pathway. The PCT publication teaches that by introducing nucleic acid molecules that encode these engineered RNA precursors into cells in vivo with appropriate regulatory sequences, expression of the engineered RNA precursors can be selectively controlled both temporally and spatially, i.e., at particular times and/or in particular tissues, organs, or cells.

International Patent Application Publication No. WO 02/44321 discloses that double-stranded RNAs (dsRNAs) of 19-23 nt in length induce sequence-specific post-transcriptional gene silencing in a *Drosophila* in vitro system. The PCT publication teaches that siRNAs duplexes can be generated by an RNase III-like processing reaction from long dsRNAs or by chemically synthesized siRNA duplexes with overhanging 3' ends mediating efficient target RNA cleavage in the lysate where the cleavage site is located near the center of the region spanned by the guiding siRNA. The PCT publication also provides evidence that the direction of dsRNA processing determines whether sense or antisense-identical target RNA can be cleaved by the produced siRNA complex. Systematic analyses of the effects of length, secondary structure, sugar backbone and sequence specificity of siRNAs on RNA interference have been disclosed to aid siRNA design. In addition, silencing efficacy has been shown to correlate with the GC content of the 5' and 3' regions of the 19 base pair target sequence. It was found that siRNAs targeting sequences with a GC rich 5' and GC poor 3' perform the best. More detailed discussion may be found in Elbashir et al., 2001, *EMBO J.* 20:6877-6888 and Aza-Blanc et al., 2003, *Mol. Cell* 12:627-637; each of which is hereby incorporated by reference herein in its entirety.

The invention provides inhibitory nucleic acids for targeting cellular components and inhibiting virus replication. In particular, the invention provides nucleic acids for cellular enzymes involved in phosphatidic acid synthesis, including GPAT, AGPAT, PLD, and DGK. These gene sequences are known in the art, and inhibitory nucleic acids are commercially available. For example, for each target of interest, Sigma-Aldrich provides several target-specific shRNAs and siRNAs.

In addition, siRNA design algorithms are disclosed in PCT publications WO 2005/018534 A2 and WO 2005/042708 A2; each of which is hereby incorporated by reference herein in its entirety. Specifically, International Patent Application Publication No. WO 2005/018534 A2 discloses methods and compositions for gene silencing using siRNA having partial sequence homology to its target gene. The application provides methods for identifying common and/or differential responses to different siRNAs targeting a gene. The application also provides methods for evaluating the relative activity of the two strands of an siRNA. The application further provides methods of using siRNAs as therapeutics for treatment of diseases. International Patent Application Publication No. WO 2005/042708 A2 provides a method for identifying siRNA target motifs in a transcript using a position-specific score matrix approach. It also provides a method for identifying off-target genes of an siRNA using a position-specific score matrix approach. The application further provides a method for designing siRNAs with improved silencing efficacy and specificity as well as a library of exemplary siRNAs.

Design software can be use to identify potential sequences within the target enzyme mRNA that can be targeted with siRNAs in the methods described herein. See, for example, http://www.ambion.com/techlib/misc/siRNA_finder.html ("Ambion siRNA Target Finder Software"). For example, the nucleotide sequences of GPAT, AGPAT, PLD, and DGK are entered into the Ambion siRNA Target Finder Software (http://www.ambion.com/techlib/misc/siRNA_finder.html), and the software identifies potential GPAT, AGPAT, PLD or DGK target sequences and corresponding siRNA sequences that can be used in assays to inhibit the aforementioned enzymes by downregulation of expression.

In certain embodiments, a compound is an siRNA effective to inhibit expression of a target enzyme (e.g., GPAT), wherein the siRNA comprises a first strand comprising a sense sequence of the target enzyme mRNA and a second strand comprising a complement of the sense sequence of the target enzyme, and wherein the first and second strands are about 21 to 23 nucleotides in length. In some embodiments, the siRNA comprises first and second strands comprise sense and complement sequences, respectively, of the target enzyme mRNA that is about 17, 18, 19, or 20 nucleotides in length.

The RNAi molecule (e.g., siRNA, shRNA, miRNA) can be both partially or completely double-stranded, and can encompass fragments of at least 18, at least 19, at least 20, at least 21, at least 22, at least 23, at least 24, at least 25, at least 30, at least 35, at least 40, at least 45, and at least 50 or more nucleotides per strand. The RNAi molecule (e.g., siRNA, shRNA, miRNA) can also comprise 3' overhangs of at least 1, at least 2, at least 3, or at least 4 nucleotides. The RNAi molecule (e.g., siRNA, shRNA, miRNA) can be of any length desired by the user as long as the ability to inhibit target gene expression is preserved.

RNAi molecules can be obtained using any of a number of techniques known to those of ordinary skill in the art. Generally, production of RNAi molecules can be carried out by chemical synthetic methods or by recombinant nucleic acid techniques. Methods of preparing a dsRNA are described, for example, in Ausubel et al., Current Protocols in Molecular Biology (Supplement 56), John Wiley & Sons, New York (2001); Sambrook et al., Molecular Cloning: A Laboratory Manual, 3.sup.rd ed., Cold Spring Harbor Press, Cold Spring Harbor (2001); and can be employed in the methods described herein. For example, RNA can be transcribed from PCR products, followed by gel purification. Standard procedures known in the art for in vitro transcription of RNA from PCR templates. For example, dsRNA can be synthesized using a PCR template and the Ambion T7 MEGASCRIPT, or other similar, kit (Austin, Tex.); the RNA can be subsequently precipitated with LiCl and resuspended in a buffer solution.

To assay for RNAi activity in cells, any of a number of techniques known to those of ordinary skill in the art can be employed. For example, the RNAi molecules are introduced into cells, and the expression level of the target enzyme can be assayed using assays known in the art, e.g., ELISA and immunoblotting. Also, the mRNA transcript level of the target enzyme can be assayed using methods known in the art, e.g., Northern blot assays and quantitative real-time PCR. Further the activity of the target enzyme can be assayed using methods known in the art and/or described herein in Section 3. In a specific embodiment, the RNAi molecule reduces the protein expression level of the target enzyme by at least about 10%, 20%, 30%, 40%, 50%, 60%, 70%, 80%, 90%, or 95%. In one embodiment, the RNAi molecule reduces the mRNA transcript level of the target enzyme by at least about 10%, 20%, 30%, 40%, 50%, 60%, 70%, 80%, 90%, or 95%. In a particular embodiment, the RNAi molecule reduces the enzymatic activity of the target enzyme by at least about 10%, 20%, 30%, 40%, 50%, 60%, 70%, 80%, 90%, or 95%.

3. Screening Assays to Identify Inhibitors of GPAT

Compounds known to be inhibitors of GPAT can be directly screened for antiviral activity using assays known in the art and/or described infra (See, e.g., Section 4 et seq.). While optional, derivatives or congeners of such inhibitors, or any other compound can be tested for their ability to modulate the enzyme targets using assays known to those of ordinary skill in the art and/or described below. Compounds found to modulate these targets can be further tested for antiviral activity.

Alternatively, compounds can be tested directly for antiviral activity. Those compounds which demonstrate anti-viral activity, or that are known to be antiviral but have unacceptable specificity or toxicity, can be screened against the enzyme targets of the invention. Antiviral compounds that modulate the enzyme targets can be optimized for better activity profiles.

Assays to test compounds for GPAT, AGPAT, PLD, or DGK activity are known in the art (See, e.g., Wydysh et al., J. Med. Chem. (2009), 52, 3317-3327 for GPAT assays; Jain et al., J. Biol. Chem., 282 (42), 30562-30569, 2007 for AGPAT assays; Lewis et al. Bioorg. and Med. Chem. Lett., 19 (2009) 1916-1920 for PLD assays; and Topham et al., J. Cell Biol., 152 (6), 2001, 1135-1143 for DGK assays).

Any host cell enzyme that relates to an inhibitory function of GPAT, AGPAT, PLD, or DGK is also contemplated as a potential target for antiviral intervention. In some embodiments of the invention, the compound increases an enzyme's activity (for example, an enzyme that is a negative regulator of GPAT, AGPAT, PLD, or DGK might have its activity increased by a potential antiviral compound). In specific embodiments, the compound increases an enzyme's activity by at least approximately 10%, 15%, 20%, 25%, 30%, 40%, 50%, 60%, 70%, 80% or 90%. In some embodiments, the compound decreases an enzyme's activity. In particular embodiments, the compound decreases an enzyme's activity by at least approximately 10%, 15%, 20%, 25%, 30%, 40%, 50%, 60%, 70%, 80%, 90%, 95% or 100%. In certain embodiments, the compound exclusively modulates a single enzyme. In some embodiments, the compound modulates multiple enzymes, although it might modulate one enzyme to a greater extent than another. Using the standard enzyme activity assays described herein, the activity of the compounds could be characterized. In one embodiment, a compound exhibits an irreversible inhibition or activation of a particular enzyme. In some embodiments, a compound reversibly inhibits or activates an enzyme. In some embodiments, a compound alters the kinetics of the enzyme.

In one embodiment, for example, evaluating the interaction between the test compound and host target enzyme includes one or more of (i) evaluating binding of the test compound to the enzyme; (ii) evaluating a biological activity of the enzyme; (iii) evaluating an enzymatic activity (e.g., acyltransferase, lipase or kinase activity) of the enzyme in the presence and absence of test compound. The in vitro contacting can include forming a reaction mixture that includes the test compound, enzyme, any required cofactor (e.g., biotin) or energy source (e.g., ATP, or radiolabeled ATP), a substrate (e.g., acetyl-CoA, a sugar, a polypeptide, a nucleoside, or any other metabolite, with or without label) and evaluating conversion of the substrate into a product. Evaluating product formation can include, for example, detecting the transfer of carbons or phosphate (e.g., chemically or using a label, e.g., a radiolabel), detecting the reaction product, detecting a secondary reaction dependent on the first reaction, or detecting a physical property of the substrate, e.g., a change in molecular weight, charge, or pI.

Target enzymes for use in screening assays can be purified from a natural source, e.g., cells, tissues or organs comprising adipocytes (e.g., adipose tissue), liver, etc. Alternatively, target enzymes can be expressed in any of a number of different recombinant DNA expression systems and can be obtained in large amounts and tested for biological activity. For expression in recombinant bacterial cells, for example E. coli, cells are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as beta-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, biologically active target enzyme useful for screening compounds for the purposes of the invention. Alternatively, the target enzyme to be screened could be partially purified or tested in a cellular lysate or other solution or mixture.

Substrate and product levels can be evaluated in an in vitro system, e.g., in a biochemical extract, e.g., of proteins. For example, the extract may include all soluble proteins or a subset of proteins (e.g., a 70% or 50% ammonium sulfate cut), the useful subset of proteins defined as the subset that includes the target enzyme. The effect of a test compound can be evaluated, for example, by measuring substrate and product levels at the beginning of a time course, and then comparing such levels after a predetermined time (e.g., 0.5, 1, or 2 hours) in a reaction that includes the test compound and in a parallel control reaction that does not include the test compound. This is one method for determining the effect of a test compound on the substrate-to-product ratio in vitro. Reaction rates can obtained by linear regression analysis of radioactivity or other label incorporated vs. reaction time for each incubation. $K_M$ and $V_{max}$ values can be determined by nonlinear regression analysis of initial velocities, according to the standard Henri-Michaelis-Menten equation. $k_{cat}$ can be obtained by dividing $V_{max}$ values by reaction concentrations of enzyme, e.g., derived by colorimetric protein determinations (e.g., Bio-RAD protein assay, Bradford assay, Lowry method). In one embodiment, the compound irreversibly inactivates the target enzyme. In another embodiment, the compound reversibly inhibits the target enzyme. In some embodiments, the compound reversibly inhibits the target enzyme by competitive inhibition. In some embodiments, the compound reversibly inhibits the target enzyme by noncompetitive inhibition. In some embodiments, the compound reversibly inhibits the target enzyme by uncompetitive inhibition. In a further embodiment, the compound inhibits the target enzyme by mixed inhibition. The mechanism of inhibition by the compound can be determined by standard assays known by those of ordinary skill in the art.

Methods for the quantitative measurement of enzyme activity utilizing a phase partition system are described in U.S. Pat. No. 6,994,956, which is incorporated by reference herein in its entirety. Specifically, a radiolabeled substrate and the product of the reaction are differentially partitioned into an aqueous phase and an immiscible scintillation fluid-containing organic phase, and enzyme activity is assessed either by incorporation of a radiolabeled-containing organic-soluble moiety into product molecules (gain of signal assay) or loss of a radiolabel-containing organic-soluble moiety from substrate molecules (loss of signal assay). Scintillations are only detected when the radionuclide is in the organic, scintillant-containing phase. Such methods can be employed to test the ability of a compound to inhibit the activity of a target enzyme.

Cellular assays may be employed. An exemplary cellular assay includes contacting a test compound to a culture cell (e.g., a mammalian culture cell, e.g., a human culture cell) and then evaluating substrate and product levels in the cell, e.g., using any method described herein, such as Reverse Phase HPLC, LC-MS, or LC-MS/MS.

Substrate and product levels can be evaluated, e.g., by NMR, HPLC (See, e.g., Bak, M. I., and Ingwall, J. S. (1994) J. Clin. Invest. 93, 40-49), mass spectrometry, thin layer chromatography, or the use of radiolabeled components (e.g., radiolabeled ATP for a kinase assay). For example, $^{31}P$ NMR can be used to evaluate ATP and AMP levels. In one implementation, cells and/or tissue can be placed in a 10-mm NMR sample tube and inserted into a 1H/31P double-tuned probe situated in a 9.4-Tesla superconducting magnet with a bore of 89 cm. If desired, cells can be contacted with a substance that provides a distinctive peak in order to index the scans. Six $^{31}P$ NMR spectra—each obtained by signal averaging of 104 free induction decays—can be collected using a 60° flip angle, 15-microsecond pulse, 2.14-second delay, 6,000 Hz sweep width, and 2048 data points using a GE-400 Omega NMR spectrometer (Bruker Instruments, Freemont, Calif., USA). Spectra are analyzed using 20-Hz exponential multiplication and zero- and first-order phase corrections. The resonance peak areas can be fitted by Lorentzian line shapes using NMR1 software (New Methods Research Inc., Syracuse, N.Y., USA). By comparing the peak areas of fully relaxed spectra (recycle time: 15 seconds) and partially saturated spectra (recycle time: 2.14 seconds), the correction factor for saturation can be calculated for the peaks. Peak areas can be normalized to cell and/or tissue weight or number and expressed in arbitrary area units. Another method for evaluating, e.g., ATP and AMP levels includes lysing cells in a sample to form an extract, and separating the extract by Reversed Phase HPLC, while monitoring absorbance at 260 nm.

Another type of in vitro assay evaluates the ability of a test compound to modulate interaction between a first enzyme pathway component and a second enzyme pathway component This type of assay can be accomplished, for example, by coupling one of the components with a radioisotope or enzymatic label such that binding of the labeled component to the second pathway component can be determined by detecting the labeled compound in a complex. An enzyme pathway component can be labeled with $^{125}I$, $^{35}S$, $^{14}C$, or $^{3}H$, either directly or indirectly, and the radioisotope detected by direct counting of radio-emission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Soluble and/or membrane-bound forms of isolated proteins (e.g., enzyme pathway components and their receptors or biologically active portions thereof) can be used in the cell-free assays of the invention. When membrane-bound forms of the enzyme are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate. In another example, the enzyme pathway component can reside in a membrane, e.g., a liposome or other vesicle.

Cell-free assays involve preparing a reaction mixture of the target enzyme and the test compound under conditions and for a time sufficient to allow the two components to interact and bind, thus forming a complex that can be removed and/or detected. In one embodiment, the target enzyme is mixed with a solution containing one or more, and often many hundreds or thousands, of test compounds. The target enzyme, including any bound test compounds, is then isolated from unbound (i.e., free) test compounds, e.g., by size exclusion chromatography or affinity chromatography. The test compound(s) bound to the target can then be separated from the target enzyme, e.g., by denaturing the enzyme in organic solvent, and the compounds identified by appropriate analytical approaches, e.g., LC-MS/MS.

The interaction between two molecules, e.g., target enzyme and test compound, can also be detected, e.g., using a fluorescence assay in which at least one molecule is fluorescently labeled, e.g., to evaluate an interaction between a test compound and a target enzyme. One example of such an assay includes fluorescence energy transfer (FET or FRET for fluorescence resonance energy transfer) (See, for example, Lakowicz et al., U.S. Pat. No. 5,631,169; Stavrianopoulos, et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, a proteinaceous "donor" molecule may simply utilize the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) Comb Chem HTS 2:177-190; Jameson et al. (1995) Methods Enzymol 246:283; See Anal Biochem. 255:257 (1998). Fluorescence polarization can be monitored in multi-well plates. See, e.g., Parker et al. (2000) Journal of Biomolecular Screening 5 :77-88; and Shoeman, et al. (1999) 38, 16802-16809.

In another embodiment, determining the ability of the target enzyme to bind to a target molecule can be accomplished using real-time Biomolecular Interaction Analysis (BIA) (See, e.g., Sjolander, S. and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target enzyme is anchored onto a solid phase. The target enzyme/test compound complexes anchored on the solid phase can be detected at the end of the reaction, e.g., the binding reaction. For example, the target enzyme can be anchored onto a solid surface, and the test compound (which is not anchored), can be labeled, either directly or indirectly, with detectable labels discussed herein.

It may be desirable to immobilize either the target enzyme or an anti-target enzyme antibody to facilitate separation of complexed from uncomplexed forms of one or both of the proteins, as well as to accommodate automation of the assay. Binding of a test compound to target enzyme, or interaction of a target enzyme with a second component in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/target enzyme fusion proteins can be adsorbed onto glutathione sepharose beads (Sigma Chemical, St. Louis, Mo., USA) or glutathione derivatized microtiter plates, which are then combined with the test compound or the test compound and either the non-adsorbed target enzyme, and the mixture incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target enzyme binding or activity is determined using standard techniques.

Other techniques for immobilizing either a target enzyme or a test compound on matrices include using conjugation of biotin and streptavidin. Biotinylated target enzyme or test compounds can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with a target enzyme but which do not interfere with binding of the target enzyme to the test compound and/or substrate. Such antibodies can be derivatized to the wells of the plate, and unbound target enzyme trapped in the wells by antibody conjugation. Methods for detecting such complexes, in addition to those described above for the GST-immobilized complexes, include immunodetection of complexes using antibodies reactive with the target enzyme, as well as enzyme-linked assays which rely on detecting an enzymatic activity associated with the target enzyme.

Alternatively, cell free assays can be conducted in a liquid phase. In such an assay, the reaction products are separated from unreacted components, by any of a number of standard techniques, including but not limited to: differential centrifugation (See, for example, Rivas, G., and Minton, A. P., (1993) Trends Biochem Sci 18:284-7); chromatography (gel filtration chromatography, ion-exchange chromatography); electrophoresis (See, e.g., Ausubel, F. et al., eds. Current Protocols in Molecular Biology 1999, J. Wiley: New York); and immunoprecipitation (See, for example, Ausubel, F. et al., eds. (1999) Current Protocols in Molecular Biology, J. Wiley: New York). Such resins and chromatographic techniques are known to one skilled in the art (See, e.g., Heegaard, N.H., (1998) J Mol Recognit 11:141-8; Hage, D. S., and Tweed, S. A. (1997) J Chromatogr B Biomed Sci Appl. 699:499-525). Further, fluorescence energy transfer may also be conveniently utilized, as described herein, to detect binding without further purification of the complex from solution.

In a preferred embodiment, the assay includes contacting the target enzyme or biologically active portion thereof with a known compound which binds the target enzyme to form an assay mixture, contacting the assay mixture with a test compound, and determining the ability of the test compound to interact with the target enzyme, wherein determining the ability of the test compound to interact with the target enzyme includes determining the ability of the test compound to preferentially bind to the target enzyme, or to modulate the activity of the target enzyme, as compared to the known compound (e.g., a competition assay). In another embodiment, the ability of a test compound to bind to and modulate the activity of the target enzyme is compared to that of a known activator or inhibitor of such target enzyme.

The target enzymes of the invention can, in vivo, interact with one or more cellular or extracellular macromolecules, such as proteins, which are either heterologous to the host cell or endogenous to the host cell, and which may or may not be recombinantly expressed. For the purposes of this discussion, such cellular and extracellular macromolecules are referred to herein as "binding partners." Compounds that disrupt such interactions can be useful in regulating the activity of the target enzyme. Such compounds can include, but are not limited to molecules such as antibodies, peptides, and small molecules. In an alternative embodiment, the invention provides methods for determining the ability of the test compound to modulate the activity of a target enzyme through modulation of the activity of a downstream effector of such target enzyme. For example, the activity of the effector molecule on an appropriate target can be determined, or the binding of the effector to an appropriate target can be determined, as previously described.

To identify compounds that interfere with the interaction between the target enzyme and its cellular or extracellular binding partner(s), a reaction mixture containing the target enzyme and the binding partner is prepared, under conditions and for a time sufficient, to allow the two products to form a complex. In order to test an inhibitory compound, the reaction mixture is provided in the presence and absence of the test compound. The test compound can be initially included in the reaction mixture, or can be added at a time subsequent to the addition of the target and its cellular or extracellular binding partner. Control reaction mixtures are incubated without the test compound or with a placebo. The formation of any complexes between the target product and the cellular or extracellular binding partner is then detected. The formation of a complex in the control reaction, but not in the reaction mixture containing the test compound, indicates that the compound interferes with the interaction of the target product and the interactive binding partner. Additionally, complex formation within reaction mixtures containing the test compound and normal target enzyme can also be compared to complex formation within reaction mixtures containing the test compound and mutant target enzyme. This comparison can be important in those cases wherein it is desirable to identify compounds that disrupt interactions of mutant but not normal target enzymes.

The assays described herein can be conducted in a heterogeneous or homogeneous format. Heterogeneous assays involve anchoring either the target enzyme or the binding partner, substrate, or tests compound onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target enzyme and a binding partners or substrate, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target enzyme or the interactive cellular or extracellular binding partner or substrate, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target enzyme and the interactive cellular or extracellular binding partner product or substrate is prepared in that either the target enzyme or their binding partners or substrates are labeled, but the signal generated by the label is quenched due to complex formation (See, e.g., U.S. Pat. No. 4,109,496 that utilizes this approach for immunoassays). The addition of a test substance that competes with and displaces one of the species from the preformed complex will result in the generation of a signal above background. In this way, test compounds that disrupt target enzyme-binding partner or substrate contact can be identified.

In yet another aspect, the target enzyme can be used as "bait protein" in a two-hybrid assay or three-hybrid assay (See, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent, International patent application Publication No. WO94/10300), to identify other proteins that bind to or interact with target enzyme ("target enzyme binding protein" or "target enzyme-bp") and are involved in target enzyme pathway activity. Such target enzyme-bps can be activators or inhibitors of the target enzyme or target enzyme targets as, for example, downstream elements of the target enzyme pathway.

In another embodiment, modulators of a target enzyme's gene expression are identified. For example, a cell or cell free mixture is contacted with a candidate compound and the expression of the target enzyme mRNA or protein evaluated relative to the level of expression of target enzyme mRNA or protein in the absence of the candidate compound. When expression of the target enzyme component mRNA or protein is greater in the presence of the candidate compound than in its absence, the candidate compound is identified as a stimulator of target enzyme mRNA or protein expression. Alternatively, when expression of the target enzyme mRNA or protein is less (statistically significantly less) in the presence of the candidate compound than in its absence, the candidate compound is identified as an inhibitor of the target enzyme mRNA or protein expression. The level of the target enzyme mRNA or protein expression can be determined by methods for detecting target enzyme mRNA or protein, e.g., Westerns, Northerns, PCR, mass spectroscopy, 2-D gel electrophoresis, and so forth, all which are known to those of ordinary skill in the art.

Mass spectrometry can be utilized for determination of metabolite levels and enzymatic activity. The levels of specific metabolites (e.g. AMP, ATP) can be quantified by liquid chromatography-mass spectrometry (LC-MS). A metabolite of interest will have a specific chromatographic retention time at which point the mass spectrometer performs a selected reaction monitoring scan event (SRM) that consists of three identifiers:

1) The metabolite's mass (the parent ion);
2) The energy required to fragment the parent ion in a collision with argon to yield a fragment with a specific mass; and
3) The mass of the specific fragment ion.

Utilizing the above identifiers, the accumulation of a metabolite can be measured whose production depends on the activity of a metabolic enzyme of interest. By adding an excess of enzyme substrate to a cellular lysate, so as to make the activity of the enzyme rate limiting, the accumulation of enzymatic product over time is then measured by LC-MS/MS as outlined above, and serves as a function of the metabolic enzyme's activity. An example of such an assay is reported in Munger et al, 2006 PLoS Pathogens, 2: 1-11, incorporated herein by reference in its entirety, in which the activity of phosphofructokinase present in infected lysates was measured by adding an excess of the phosphofructokinase substrates ATP and fructose phosphate and measuring fructose bisphosphate accumulation by LC-MS/MS. This approach can be adopted to measure the activities of numerous host target enzymes.

3.1 Compounds

A compound of interest can be tested for its ability to modulate the activity of GPAT. Once such compounds are identified as having GPAT-modulating activity, they can be further tested for their antiviral activity as described in Section 4. Alternatively, compounds can be screened for antiviral activity and optionally characterized using the GPAT screening assays described herein.

In one embodiment, high throughput screening methods are used to provide a combinatorial chemical or peptide library (e.g., a publicly available library) containing a large number of potential therapeutic compounds (potential modulators or ligand compounds). Such "combinatorial chemical libraries" or "ligand libraries" are then screened in one or more assays, as described in Section 3 herein, to identify those library members (particular chemical species or subclasses) that display a desired characteristic activity, e.g., inhibition of GPAT activity). The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (See, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (See Ausubel, Berger and Sambrook, all supra), peptide nucleic acid libraries (See, e.g., U.S. Pat. No. 5,539,083), antibody libraries (See, e.g., Vaughn et al., Nature Biotechnology, 14(3):309-314 (1996) and PCT/US96/10287), carbohydrate libraries (See, e.g., Liang et al., Science, 274:1520-1522 (1996) and International Patent Application Publication NO. WO 1997/000271), small organic molecule libraries (See, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework). Devices for the preparation of combinatorial libraries are commercially available (See, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (See, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.). The test compounds can also be obtained from: biological libraries; peptoid libraries (libraries of molecules having the functionalities of peptides, but with a novel, non-peptide backbone which are resistant to enzymatic degradation but which nevertheless remain bioactive; See, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) Anticancer Drug Des. 12:145). A library of proteins may be produced by an expression library or a display library (e.g., a phage display library). Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc. Natl. Acad. Sci. USA 89:1865-1869) or on phage (Scott and Smith (1990) Science 249:386-390; Devlin (1990) Science 249: 404-406; Cwirla et al. (1990) Proc. Natl. Acad. Sci. 87:6378-6382; Felici (1991) J. Mol. Biol. 222:301-310; Ladner supra.). Enzymes can be screened for identifying compounds which can be selected from a combinatorial chemical library or any other suitable source (Hogan, Jr., Nat. Biotechnology 15:328, 1997).

Any assay herein, e.g., an in vitro assay or an in vivo assay, can be performed individually, e.g., just with the test compound, or with appropriate controls. For example, a parallel assay without the test compound, or other parallel assays without other reaction components, e.g., without a target or without a substrate. Alternatively, it is possible to compare assay results to a reference, e.g., a reference value, e.g., obtained from the literature, a prior assay, and so forth. Appropriate correlations and art known statistical methods can be used to evaluate an assay result.

Once a compound is identified as having a desired effect, production quantities of the compound can be synthesized, e.g., producing at least 50 mg, 500 mg, 5 g, or 500 g of the compound. Although a compound that is able to penetrate a host cell is preferable in the practice of the invention, a compound may be combined with solubilizing agents or administered in combination with another compound or compounds to maintain its solubility, or help it enter a host cell, e.g., by mixture with lipids. The compound can be formulated, e.g., for administration to a subject, and may also be administered to the subject.

4. Characterization of Antiviral Activity of Compounds 4.1 Viruses

The present invention provides compounds for use in the prevention, management and/or treatment of viral infection. The antiviral activity of compounds against any virus can be tested using techniques described in Section 4.2 herein below. The virus may be enveloped or naked, have a DNA or RNA genome, or have a double-stranded or single-stranded genome. In specific embodiments, the virus infects humans. In other embodiments, the virus infects non-human animals. In a specific embodiment, the virus infects pigs, fowl, other livestock, or pets.

In certain embodiments, the virus is an enveloped virus. Enveloped viruses include, but are not limited to viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Non-limiting examples of viruses that belong to these families are included in Table 1.

TABLE 1

Families of Enveloped Viruses

| Virus Family | Members |
| --- | --- |
| Hepadnavirus (Hepadnaviridae) | hepatitis B virus (HBV), woodchuck hepatitis virus, ground squirrel hepatitis virus, duck hepatitis B virus, heron hepatitis B virus |
| Herpesvirus (Herpesviridae) | herpes simplex virus (HSV) types 1 and 2, varicella-zoster virus, cytomegalovirus (CMV), human cytomegalovirus (HCMV), Epstein-Barr virus (EBV), human herpesvirus 6 (variants A and B), human herpesvirus 7, human herpesvirus 8, Kaposi's sarcoma - associated herpes virus (KSHV), B virus |
| Poxvirus (Poxviridae) | vaccinia virus, variola virus, smallpox virus, monkeypox virus, cowpox virus, camelpox virus, mousepox virus, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus |
| Flavivirus (Flaviviridae) | dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus |
| Togavirus (Togaviridae) | Venezuelan equine encephalitis virus, chikungunya virus, Ross River virus, Mayaro virus, Sindbis virus, rubella virus |
| Retrovirus (Retroviridae) | human immunodeficiency virus (HIV) types 1 and 2, human T cell leukemia virus (HTLV) types 1, 2, and 5, mouse mammary tumor virus (MMTV), Rous sarcoma virus (RSV), lentiviruses |
| Coronavirus (Coronaviridae) | severe acute respiratory syndrome (SARS) virus |
| Filovirus (Filoviridae) | Ebola virus, Marburg virus |
| Rhabdovirus (Rhabdoviridae) | rabies virus, vesicular stomatitis virus |
| Bunyavirus (Bunyaviridae) | Crimean-Congo hemorrhagic fever virus, Rift Valley fever virus, La Crosse virus, Hantaan virus |
| Orthomyxovirus (Orthomyxoviridae) | influenza virus (types A, B, and C) |
| Paramyxovirus (Paramyxoviridae) | parainfluenza virus, respiratory syncytial virus (types A and B), measles virus, mumps virus |
| Arenavirus (Arenaviridae) | lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, Tamiami virus |

In some embodiments, the virus is a non-enveloped virus, i.e., the virus does not have an envelope and is naked. Non-limiting examples of such viruses include viruses that are members of the parvovirus family, circovirus family, polyoma virus family, papillomavirus family, adenovirus family, iridovirus family, reovirus family, birnavirus family, calicivirus family, and picornavirus family. Examples of viruses that belong to these families include, but are not limited to, those set forth in Table 2.

TABLE 2

Families of Non-Enveloped (Naked) Viruses

| Virus Family | Members |
| --- | --- |
| Parvovirus (Parvoviridae) | canine parvovirus, parvovirus B19 |
| Circovirus (Circoviridae) | porcine circovirus type 1 and 2, BFDV (Beak and Feather Disease Virus), chicken anaemia virus |
| Polyomavirus (Polyomaviridae) | simian virus 40 (SV40), JC virus, BK virus, Budgerigar fledgling disease virus |
| Papillomavirus (Papillomaviridae) | human papillomavirus, bovine papillomavirus (BPV) type 1 |
| Adenovirus (Adenoviridae) | human adenovirus (HAdV-A, HAdV-B, HAdV-C, HAdV-D, HAdV-E, and HAdV-F), fowl adenovirus A, ovine adenovirus D, frog adenovirus |
| Reovirus (Reoviridae) | human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1 |
| Birnavirus (Birnaviridae) | bursal disease virus, pancreatic necrosis virus |

TABLE 2-continued

Families of Non-Enveloped (Naked) Viruses

| Virus Family | Members |
|---|---|
| Calicivirus (Caliciviridae) | swine vesicular exanthema virus, rabbit hemorrhagic disease virus, Norwalk virus, Sapporo virus |
| Picornavirus (Picornaviridae) | human polioviruses (1-3), human coxsackieviruses A1-22, 24 (CA1-22 and CA24, CA23 = echovirus 9), human coxsackieviruses (B1-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardioviruses, aphthoviruses, echoviruses |

In certain embodiments, the virus is a DNA virus. In other embodiments, the virus is a RNA virus. In one embodiment, the virus is a DNA or a RNA virus with a single-stranded genome. In another embodiment, the virus is a DNA or a RNA virus with a double-stranded genome.

In some embodiments, the virus has a linear genome. In other embodiments, the virus has a circular genome. In some embodiments, the virus has a segmented genome. In other embodiments, the virus has a non-segmented genome.

In some embodiments, the virus is a positive-stranded RNA virus. In other embodiments, the virus is a negative-stranded RNA virus. In one embodiment, the virus is a segmented, negative-stranded RNA virus. In another embodiment, the virus is a non-segmented negative-stranded RNA virus.

In some embodiments, the virus is an icosahedral virus. In other embodiments, the virus is a helical virus. In yet other embodiments, the virus is a complex virus.

In certain embodiments, the virus is a herpes virus, e.g., HSV-1, HSV-2, and CMV. In other embodiments, the virus is not a herpes virus (e.g., HSV-1, HSV-2, and CMV). In a specific embodiment, the virus is HSV. In an alternative embodiment, the virus is not HSV. In another embodiment, the virus is HCMV. In a further alternative embodiment, the virus is not HCMV. In another embodiment, the virus is a liver trophic virus. In an alternative embodiment, the virus is not a liver trophic virus. In another embodiment, the virus is a hepatitis virus. In an alternate embodiment, the virus is not a hepatitis virus. In another embodiment, the virus is a hepatitis C virus. In a further alternative embodiment, the virus is not a hepatitis C virus. In another specific embodiment, the virus is an influenza virus. In an alternative embodiment, the virus is not an influenza virus. In some embodiments, the virus is a retrovirus. In some embodiments, the virus is not a retrovirus. In some embodiments, the virus is HIV. In other embodiments, the virus is not HIV. In certain embodiments, the virus is a hepatitis B virus. In another alternative embodiment, the virus is not a hepatitis B virus. In a specific embodiment, the virus is EBV. In a specific alternative embodiment, the virus is not EBV. In some embodiments, the virus is Kaposi's sarcoma-associated herpes virus (KSHV). In some alternative embodiments, the virus is not KSHV. In certain embodiments the virus is a variola virus. In certain alternative embodiments, the virus is not variola virus. In one embodiment, the virus is a Dengue virus. In one alternative embodiment, the virus is not a Dengue virus. In other embodiments, the virus is a SARS virus. In other alternative embodiments, the virus is not a SARS virus. In a specific embodiment, the virus is an Ebola virus. In an alternative embodiment, the virus is not an Ebola virus. In some embodiments the virus is a Marburg virus. In an alternative embodiment, the virus is not a Marburg virus. In certain embodiments, the virus is a measles virus. In some alternative embodiments, the virus is not a measles virus. In particular embodiments, the virus is a vaccinia virus. In alternative embodiments, the virus is not a vaccinia virus. In some embodiments, the virus is varicella-zoster virus (VZV). In an alternative embodiment the virus is not VZV. In some embodiments, the virus is a picornavirus. In alternative embodiments, the virus is not a picornavirus. In certain embodiments the virus is not a rhinovirus. In certain embodiments, the virus is a poliovirus. In alternative embodiments, the virus is not a poliovirus. In some embodiments, the virus is an adenovirus. In alternative embodiments, the virus is not adenovirus. In particular embodiments, the virus is a coxsackievirus (e.g., coxsackievirus B3). In other embodiments, the virus is not a coxsackievirus (e.g., coxsackievirus B3). In some embodiments, the virus is a rhinovirus. In other embodiments, the virus is not a rhinovirus. In certain embodiments, the virus is a human papillomavirus (HPV). In other embodiments, the virus is not a human papillomavirus. In certain embodiments, the virus is a virus selected from the group consisting of the viruses listed in Tables 1 and 2. In other embodiments, the virus is not a virus selected from the group consisting of the viruses listed in Tables 1 and 2. In one embodiment, the virus is not one or more viruses selected from the group consisting of the viruses listed in Tables 1 and 2.

The antiviral activities of compounds against any type, subtype or strain of virus can be assessed. For example, the antiviral activity of compounds against naturally occurring strains, variants or mutants, mutagenized viruses, reassortants and/or genetically engineered viruses can be assessed.

The lethality of certain viruses, the safety issues concerning working with certain viruses and/or the difficulty in working with certain viruses may preclude (at least initially) the characterization of the antiviral activity of compounds on such viruses. Under such circumstances, other animal viruses that are representative of such viruses may be utilized. For example, SIV may be used initially to characterize the antiviral activity of compounds against HIV. Further, Pichinde virus may be used initially to characterize the antiviral activity of compounds against Lassa fever virus.

In some embodiments, the virus achieves peak titer in cell culture or a subject in 4 hours or less, 6 hours or less, 8 hours or less, 12 hours or less, 16 hours or less, or 24 hours or less. In other embodiments, the virus achieves peak titers in cell culture or a subject in 48 hours or less, 72 hours or less, or 1 week or less. In other embodiments, the virus achieves peak titers after about more than 1 week. In accordance with these embodiments, the viral titer may be measured in the infected tissue or serum.

In some embodiments, the virus achieves in cell culture a viral titer of $10^4$ pfu/ml or more, $5 \times 10^4$ pfu/ml or more, $10^5$ pfu/ml or more, $5 \times 10^5$ pfu/ml or more, $10^6$ pfu/ml or more, $5 \times 10^6$ pfu/ml or more, $10^7$ pfu/ml or more, $5 \times 10^7$ pfu/ml or more, $10^8$ pfu/ml or more, $5 \times 10^8$ pfu/ml or more, $10^9$ pfu/ml or more, $5 \times 10^9$ pfu/ml or more, or $10^{10}$ pfu/ml or more. In certain embodiments, the virus achieves in cell culture a viral titer of $10^4$ pfu/ml or more, $5 \times 10^4$ pfu/ml or more, $10^5$ pfu/ml or more, $5 \times 10^5$ pfu/ml or more, $10^6$ pfu/ml or more, $5 \times 10^6$ pfu/ml or more, $10^7$ pfu/ml or more, $5 \times 10^7$ pfu/ml or more, $10^8$ pfu/ml or more, $5 \times 10^8$ pfu/ml or more, $10^9$ pfu/ml or more, $5 \times 10^9$ pfu/ml or more, or $10^{10}$ pfu/ml or more within 4 hours, 6 hours, 8 hours, 12 hours, 16 hours, or 24 hours or less. In other embodiments, the virus achieves in cell culture a viral titer of $10^4$ pfu/ml or more, $5 \times 10^4$ pfu/ml or more, $10^5$ pfu/ml or more, $5 \times 10^5$ pfu/ml or more, $10^6$ pfu/ml or more, $5 \times 10^6$ pfu/ml or more, $10^7$ pfu/ml or more, $5 \times 10^7$ pfu/ml or more, $10^8$ pfu/ml or more, $5 \times 10^8$ pfu/ml or more, $10^9$ pfu/ml or more, $5 \times 10^9$ pfu/ml or more, or $10^{10}$ pfu/ml or more within 48 hours, 72 hours, or 1 week.

In some embodiments, the virus achieves a viral yield of 1 pfu/ml or more, 10 pfu/ml or more, $5 \times 10^1$ pfu/ml or more, $10^2$ pfu/ml or more, $5 \times 10^2$ pfu/ml or more, $10^3$ pfu/ml or more, $2.5 \times 10^3$ pfu/ml or more, $5 \times 10^3$ pfu/ml or more, $10^4$ pfu/ml or more, $2.5 \times 10^4$ pfu/ml or more, $5 \times 10^4$ pfu/ml or more, or $10^5$ pfu/ml or more in a subject. In certain embodiments, the virus achieves a viral yield of 1 pfu/ml or more, 10 pfu/ml or more, $5 \times 10^1$ pfu/ml or more, $10^2$ pfu/ml or more, $5 \times 10^2$ pfu/ml or more, $10^3$ pfu/ml or more, $2.5 \times 10^3$ pfu/ml or more, $5 \times 10^3$ pfu/ml or more, $10^4$ pfu/ml or more, $2.5 \times 10^4$ pfu/ml or more, $5 \times 10^4$ pfu/ml or more, or $10^5$ pfu/ml or more in a subject within 4 hours, 6 hours, 8 hours, 12 hours, 16 hours, 24 hours, or 48 hours. In certain embodiments, the virus achieves a viral yield of 1 pfu/ml or more, 10 pfu/ml or more, $10^1$ pfu/ml or more, $5 \times 10^1$ pfu/ml or more, $10^2$ pfu/ml or more, $5 \times 10^2$ pfu/ml or more, $10^3$ pfu/ml or more, $2.5 \times 10^3$ pfu/ml or more, $5 \times 10^3$ pfu/ml or more, $10^4$ pfu/ml or more, $2.5 \times 10^4$ pfu/ml or more, $5 \times 10^4$ pfu/ml or more, or $10^5$ pfu/ml or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 pfu or more, 10 pfu or more, $5 \times 10^1$ pfu or more, $10^2$ pfu or more, $5 \times 10^2$ pfu or more, $10^3$ pfu or more, $2.5 \times 10^3$ pfu or more, $5 \times 10^3$ pfu or more, $10^4$ pfu or more, $2.5 \times 10^4$ pfu or more, $5 \times 10^4$ pfu or more, or $10^5$ pfu or more in a subject. In certain embodiments, the virus achieves a viral yield of 1 pfu or more, 10 pfu or more, $5 \times 10^1$ pfu or more, $10^2$ pfu or more, $5 \times 10^2$ pfu or more, $10^3$ pfu or more, $2.5 \times 10^3$ pfu or more, $5 \times 10^3$ pfu or more, $10^4$ pfu or more, $2.5 \times 10^4$ pfu or more, $5 \times 10^4$ pfu or more, or $10^5$ pfu or more in a subject within 4 hours, 6 hours, 8 hours, 12 hours, 16 hours, 24 hours, or 48 hours. In certain embodiments, the virus achieves a viral yield of 1 pfu or more, 10 pfu or more, $10^1$ pfu or more, $5 \times 10^1$ pfu or more, $10^2$ pfu or more, $5 \times 10^2$ pfu or more, $10^3$ pfu or more, $2.5 \times 10^3$ pfu or more, $5 \times 10^3$ pfu or more, $10^4$ pfu or more, $2.5 \times 10^4$ pfu or more, $5 \times 10^4$ pfu or more, or $10^5$ pfu or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 infectious unit or more, 10 infectious units or more, $5 \times 10^1$ infectious units or more, $10^2$ infectious units or more, $5 \times 10^2$ infectious units or more, $10^3$ infectious units or more, $2.5 \times 10^3$ infectious units or more, $5 \times 10^3$ infectious units or more, $10^4$ infectious units or more, $2.5 \times 10^4$ infectious units or more, $5 \times 10^4$ infectious units or more, or $10^5$ infectious units or more in a subject. In certain embodiments, the virus achieves a viral yield of 1 infectious unit or more, 10 infectious units or more, $5 \times 10^1$ infectious units or more, $10^2$ infectious units or more, $5 \times 10^2$ infectious units or more, $10^3$ infectious units or more, $2.5 \times 10^3$ infectious units or more, $5 \times 10^3$ infectious units or more, $10^4$ infectious units or more, $2.5 \times 10^4$ infectious units or more, $5 \times 10^4$ infectious units or more, or $10^5$ infectious units or more in a subject within 4 hours, 6 hours, 8 hours, 12 hours, 16 hours, 24 hours, or 48 hours. In certain embodiments, the virus achieves a viral yield of 1 infectious unit or more, 10 infectious units or more, $10^1$ infectious units or more, $5 \times 10^1$ infectious units or more, $10^2$ infectious units or more, $5 \times 10^2$ infectious units or more, $10^3$ infectious units or more, $2.5 \times 10^3$ infectious units or more, $5 \times 10^3$ infectious units or more, $10^4$ infectious units or more, $2.5 \times 10^4$ infectious units or more, $5 \times 10^4$ infectious units or more, or $10^5$ infectious units or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed. In a specific embodiment, the virus achieves a yield of less than $10^4$ infectious units. In other embodiments the virus achieves a yield of $10^5$ or more infectious units.

In some embodiments, the virus achieves a viral titer of 1 infectious unit per ml or more, 10 infectious units per ml or more, $5 \times 10^1$ infectious units per ml or more, $10^2$ infectious units per ml or more, $5 \times 10^2$ infectious units per ml or more, $10^3$ infectious units per ml or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject. In certain embodiments, the virus achieves a viral titer of 10 infectious units per ml or more, $5 \times 10^1$ infectious units per ml or more, $10^2$ infectious units per ml or more, $5 \times 10^2$ infectious units per ml or more, $10^3$ infectious units per ml or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject within 4 hours, 6 hours, 8 hours, 12 hours, 16 hours, 24 hours, or 48 hours. In certain embodiments, the virus achieves a viral titer of 1 infectious unit per mL or more, 10 infectious units per ml or more, $5 \times 10^1$ infectious units per ml or more, $10^2$ infectious units per ml or more, $5 \times 10^2$ infectious units per ml or more, $10^3$ infectious units per mL or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject within 48 hours, 72 hours, or 1 week. In accordance with these embodiments, the viral titer may be measured in the infected tissue or serum. In a specific embodiment, the subject is immunocompetent. In another embodiment, the subject is immunocompromised or immunosuppressed. In a specific embodiment, the virus achieves a titer of less than $10^4$ infectious units per ml. In some embodiments, the virus achieves $10^5$ or more infectious units per ml.

In some embodiments, the virus infects a cell and produces, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell. In certain embodiments, the virus infects a cell and produces 10 or more, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell within 4 hours, 6 hours, 8 hours, 12 hours, 16 hours, or 24 hours. In other embodiments, the virus infects a cell and produces 10 or more, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell within 48 hours, 72 hours, or 1 week.

In other embodiments, the virus is latent for a period of about at least 1 day, 2 days, 3 days, 4 days, 5 days, 6 days, 7 days, 8 days, 9 days, 10 days, 11 days, 12 days, 13 days, 14 days, or 15 days. In another embodiment, the virus is latent for a period of about at least 1 week, or 2 weeks, 3 weeks, 4 weeks, 5 weeks, 6 weeks, 7 weeks, 8 weeks, 9 weeks, or 10 weeks. In a further embodiment, the virus is latent for a period of about at least 1 month, 2 months, 3 months, 4 months, 5 months, 6 months, 7 months, 8 months, 9 months, 10 months, or 11 months. In yet another embodiment, the virus is latent for a period of about at least 1 year, 2 years, 3 years, 4 years, 5 years, 6 years, 7 years, 8 years, 9 years, 10 years, 11 years, 12 years, 13 years, 14 years, or 15 years. In some embodiments, the virus is latent for a period of greater than 15 years.

4.2 In Vitro Assays to Detect Antiviral Activity

The antiviral activity of compounds may be assessed in various in vitro assays described herein or others known to one of skill in the art. Non-limiting examples of the viruses that can be tested for compounds with antiviral activities against such viruses are provided in Section 4.1, supra. In specific embodiments, compounds exhibit an activity profile that is consistent with their ability to inhibit viral replication while maintaining low toxicity with respect to eukaryotic cells, preferably mammalian cells. For example, the effect of a compound on the replication of a virus may be determined by infecting cells with different dilutions of a virus in the presence or absence of various dilutions of a compound, and assessing the effect of the compound on, e.g., viral replication, viral genome replication, and/or the synthesis of viral proteins. Alternatively, the effect of a compound on the replication of a virus may be determined by contacting cells with various dilutions of a compound or a placebo, infecting the cells with different dilutions of a virus, and assessing the effect of the compound on, e.g., viral replication, viral genome replication, and/or the synthesis of viral proteins. Altered viral replication can be assessed by, e.g., plaque formation. The production of viral proteins can be assessed by, e.g., ELISA, Western blot, immunofluorescence, or flow cytometry analysis. The production of viral nucleic acids can be assessed by, e.g., RT-PCR, PCR, Northern blot analysis, or Southern blot.

In certain embodiments, compounds reduce the replication of a virus by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, compounds reduce the replication of a virus by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, compounds reduce the replication of a virus by about at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, compounds reduce the replication of a virus by about 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such compounds may be further assessed for their safety and efficacy in assays such as those described in Section 4, infra.

In certain embodiments, compounds reduce the replication of a viral genome by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, compounds reduce the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, compounds reduce the replication of a viral genome by about at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, compounds reduce the replication of a viral genome by about 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such compounds may be further assessed for their safety and efficacy in assays such as those described in Section 4, infra.

In certain embodiments, compounds reduce the synthesis of viral proteins by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, compounds reduce the synthesis of viral proteins by approximately at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, compounds reduce the synthesis of viral proteins by approximately at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, compounds reduce the synthesis of viral proteins by approximately 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such compounds may be further assessed for their safety and efficacy in assays such as those described in Section 4, infra.

In some embodiments, compounds result in about a 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more inhibition/reduction of viral yield per round of viral replication. In certain embodiments, compounds result in about a 2 fold or more reduction inhibition/reduction of viral yield per round of viral replication. In specific embodiments, compounds result in about a 10 fold or more inhibition/reduction of viral yield per round of viral replication.

The in vitro antiviral assays can be conducted using any eukaryotic cell, including primary cells and established cell lines. The cell or cell lines selected should be susceptible to infection by a virus of interest. Non-limiting examples of mammalian cell lines that can be used in standard in vitro antiviral assays (e.g., viral cytopathic effect assays, neutral red update assays, viral yield assay, plaque reduction assays) for the respective viruses are set out in Table 3.

TABLE 3

Examples of Mammalian Cell Lines in Antiviral Assays

| Virus | Cell Line |
| --- | --- |
| herpes simplex virus (HSV) | primary fibroblasts (MRC-5 cells) |
| | Vero cells |
| human cytomegalovirus (HCMV) | primary fibroblasts (MRC-5 cells) |
| Influenza | primary fibroblasts (MRC-5 cells) |
| | Madin Darby canine kidney (MDCK) |
| | primary chick embryo |
| | chick kidney |
| | calf kidney |
| | African green monkey kidney (Vero) cells |
| | mink lung |
| | human respiratory epithelia cells |
| hepatitis C virus | Huh7 (or Huh7.7) |
| | primary human hepatocytes (PHH) |
| | immortalized human hepatocytes (IHH) |
| HIV-1 | MT-2 cells (T cells) |
| Dengue virus | Vero cells |
| Measles virus | African green monkey kidney (CV-1) cells |
| SARS virus | Vero 76 cells |
| Respiratory syncytial virus | African green monkey kidney (MA-104) cells |
| Venezuelan equine encephalitis virus | Vero cells |
| West Nile virus | Vero cells |
| Yellow fever virus | Vero cells |
| HHV-6 | Cord Blood Lymphocytes (CBL) |
| | Human T cell lymphoblastoid cell lines (HSB-2 and SupT-1) |
| HHV-8 | B-cell lymphoma cell line (BCBL-1) |
| EBV | umbilical cord blood lymphocytes |

Sections 4.2.1 to 4.2.7 below provide non-limiting examples of antiviral assays that can be used to characterize the antiviral activity of compounds against the respective virus. One of skill in the art will know how to adapt the methods described in Sections 4.2.1 to 4.2.7 to other viruses by, e.g., changing the cell system and viral pathogen, such as described in Table 3.

4.2.1 Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei). For adenovirus infection, crystalline arrays of adenovirus capsids accumulate in the nucleus to form an inclusion body.

The CPE assay can provide a measure of the antiviral effect of a compound. In a non-limiting example of such an assay, compounds are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). CPE is read microscopically after a known positive control drug is evaluated in parallel with compounds in each test. Non-limiting examples of positives controls are ribavirin for dengue, influenza, measles, respiratory syncytial, parainfluenza, Pichinde, Punta Toro and Venezuelan equine encephalitis viruses; cidofovir for adenovirus; pirodovir for rhinovirus; 6-azauridine for West Nile and yellow fever viruses; and alferon (interferon α-n3) for SARS virus. The data are expressed as 50% effective concentrations or approximated virus-inhibitory concentration, 50% endpoint (EC50) and cell-inhibitory concentration, 50% endpoint (IC50). General selectivity index ("SI") is calculated as the IC50 divided by the EC50. These values can be calculated using any method known in the art, e.g., the computer software program MacSynergy II by M. N. Prichard, K. R. Asaltine, and C. Shipman, Jr., University of Michigan, Ann Arbor, Mich.

In one embodiment, a compound has an SI of greater than 3, or 4, or 5, or 6, or 7, or 8, or 9, or 10, or 11, or 12, or 13, or 14, or 15, or 20, or 21, or 22, or 23, or 24, or 25, or 30, or 35, or 40, or 45, or 50, or 60, or 70, or 80, or 90, or 100, or 200, or 300, or 400, or 500, 1,000, or 10,000. In some embodiments, a compound has an SI of greater than 10. In a specific embodiment, compounds with an SI of greater than 10 are further assessed in other in vitro and in vivo assays described herein or others known in the art to characterize safety and efficacy.

4.2.2 Neutral Red (NR) Dye Uptake Assay

The NR Dye Uptake assay can be used to validate the CPE inhibition assay (See Section 4.2.1). In a non-limiting example of such an assay, the same 96-well microplates used for the CPE inhibition assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus et al., Appl. Environment. Microbiol. 31:35-38, 1976). An EC50 is determined for samples with infected cells and contacted with compounds, and an IC50 is determined for samples with uninfected cells contacted with compounds.

4.2.3 Virus Yield Assay

Lysed cells and supernatants from infected cultures such as those in the CPE inhibition assay (See Section 4.2.1) can be used to assay for virus yield (production of viral particles after the primary infection). In a non-limiting example, these supernatants are serial diluted and added onto monolayers of susceptible cells (e.g., Vero cells). Development of CPE in these cells is an indication of the presence of infectious viruses in the supernatant. The 90% effective concentration (EC90), the test compound concentration that inhibits virus yield by 1 $\log_{10}$, is determined from these data using known calculation methods in the art. In one embodiment, the $EC_{90}$ of compound is at least 1.5 fold, 2 fold, 3 fold, 4 fold, 5 fold, 6 fold, 7 fold, 8 fold, 9 fold, 10 fold, 20 fold, 30 fold, 40 fold, or 50 fold less than the EC90 of the negative control sample.

4.2.4 Plaque Reduction Assay

In a non-limiting example of such an assay, the virus is diluted into various concentrations and added to each well containing a monolayer of the target mammalian cells in triplicate. The plates are then incubated for a period of time to achieve effective infection of the control sample (e.g., 1 hour with shaking every fifteen minutes). After the incubation period, an equal amount of 1% agarose is added to an equal volume of each compound dilution prepared in 2× concentration. In certain embodiments, final compound concentrations between 0.03 μg/ml to 100 μg/ml can be tested with a final agarose overlay concentration of 0.5%. The drug agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

4.2.5 Virus Titer Assay

In this non-limiting example, a monolayer of the target mammalian cell line is infected with different amounts (e.g., multiplicity of 3 plaque forming units (pfu) or 5 pfu) of virus (e.g., HCMV or HSV) and subsequently cultured in the presence or absence of various dilutions of compounds (e.g., 0.1 μg/ml, 1 μg/ml, 5 μg/ml, or 10 μg/ml). Infected cultures are harvested 48 hours or 72 hours post infection and titered by standard plaque assays known in the art on the appropriate target cell line (e.g., Vero cells, MRCS cells). In certain embodiments, culturing the infected cells in the presence of compounds reduces the yield of infectious virus by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to culturing the infected cells in the absence of compounds. In a specific embodiment, culturing the infected cells in the presence of compounds reduces the PFU/ml by at least 10 fold relative to culturing the infected cells in the absence of compounds.

In certain embodiments, culturing the infected cells in the presence of compounds reduces the yield of infectious virus by at least 0.5 log 10, 1 log 10, 1.5 log 10, 2 log 10, 2.5 log 10, 3 log 10, 3.5 log 10, 4 log 10, 4.5 log 10, 5 log 10, 5.5 log 10, 6 log 10, 6.5 log 10, 7 log 10, 7.5 log 10, 8 log 10, 8.5 log 10, or 9 log 10 relative to culturing the infected cells in the absence of compounds. In a specific embodiment, culturing the infected cells in the presence of compounds reduces the yield of infectious virus by at least 1 log 10 or 2 log 10 relative to culturing the infected cells in the absence of compounds. In another specific embodiment, culturing the infected cells in the presence of compounds reduces the yield of infectious virus by at least 2 log 10 relative to culturing the infected cells in the absence of compounds.

4.2.6 Flow Cytometry Assay

Flow cytometry can be utilized to detect expression of virus antigens in infected target cells cultured in the presence or absence of Compounds (See, e.g., McSharry et al., Clinical Microbiology Rev., 1994, 7:576-604). Non-limiting examples of viral antigens that can be detected on cell surfaces by flow cytometry include, but are not limited to gB, gC, gC, and gE of HSV; E protein of Japanese encephalitis; virus gp52 of mouse mammary tumor virus; gpI of varicella-zoster virus; gB of HCMV; gp160/120 of HIV; HA of influenza; gp110/60 of HHV-6; and H and F of measles virus. In other embodiments, intracellular viral antigens or viral nucleic acid can be detected by flow cytometry with techniques known in the art.

4.2.7 Genetically Engineered Cell Lines for Antiviral Assays

Various cell lines for use in antiviral assays can be genetically engineered to render them more suitable hosts for viral infection or viral replication and more convenient substrates for rapidly detecting virus-infected cells (See, e.g., Olivo, P. D., Clin. Microbiol. Rev., 1996, 9:321-334). In some aspects, these cell lines are available for testing the antiviral activity of compound on blocking any step of viral replication, such as, transcription, translation, pregenome encapsidation, reverse transcription, particle assembly and release. Nonlimiting examples of genetically engineered cells lines for use in antiviral assays with the respective virus are discussed below.

HepG2-2.2.15 is a stable cell line containing the hepatitis B virus (HBV) ayw strain genome that is useful in identifying and characterizing compounds blocking any step of viral replication, such as, transcription, translation, pregenome encapsidation, reverse transcription, particle assembly and release. In one aspect, compounds can be added to HepG2-2.2.15 culture to test whether compound will reduce the production of secreted HBV from cells utilizing real time quantitative PCR (TaqMan) assay to measure HBV DNA copies. Specifically, confluent cultures of HepG2-2.2.15 cells cultured on 96-well flat-bottomed tissue culture plates and are treated with various concentrations of daily doses of compounds. HBV virion DNA in the culture medium can be assessed 24 hours after the last treatment by quantitative blot hybridization or real time quantitative PCR (TaqMan) assay. Uptake of neutral red dye (absorbance of internalized dye at 510 nM [A510]) can be used to determine the relative level of toxicity 24 hours following the last treatment. Values are presented as a percentage of the average A510 values for separate cultures of untreated cells maintained on the same plate. Intracellular HBV DNA replication intermediates can be assessed by quantitative Southern blot hybridization. Intracellular HBV particles can be isolated from the treated HepG2-2.2.15 cells and the pregenomic RNA examined by Southern blot analysis. ELISAs can be used to quantify the amounts of the HBV envelope protein, surface antigen (HBsAg), and secreted e-antigen (HBeAg) released from cultures. Lamivudine (3TC) can be used as a positive assay control. (See Korba & Gerin, Antivir. Res. 19:55-70, 1992).

In one aspect, the cell line Huh7 ET (luc-ubi-neo/ET), which contains a new HCV RNA replicon with a stable luciferase (LUC) reporter, can be used to assay compounds antiviral activity against hepatitis C viral replication (See Krieger, N., V. Lohmann, and R. Bartenschlager J. Virol., 2001, 75:4614-4624). The activity of the LUC reporter is directly proportional to HCV RNA levels and positive control antiviral compounds behave comparably using either LUC or RNA endpoints. Subconfluent cultures of Huh7 ET cells are plated onto 96-well plates, compounds are added to the appropriate wells the next day, and the samples as well as the positive (e.g., human interferon-alpha 2b) and negative control samples are processed 72 hr later when the cells are still subconfluent. The HCV RNA levels can also be assessed using quantitative PCR (TaqMan). In some embodiments, compounds reduce the LUC signal (or HCV RNA levels) by 20%, 35%, 30%, 35%, 40%, 45%, 50%, 55%, 60%, 65%, 70%, 75%, 80%, 90%, or 95% or more relative to the untreated sample controls. In a preferred embodiment, compounds reduce the LUC signal (or HCV RNA levels) by 50% or more relative to the untreated cell controls. Other relevant cell culture models to study HCV have been described, e.g., See Durantel et al., J. Hepatology, 2007, 46:1-5.

The antiviral effect of compound can be assayed against EBV by measuring the level of viral capsid antigen (VCA)

production in Daudi cells using an ELISA assay. Various concentrations of compounds are tested (e.g., 50 mg/ml to 0.03 mg/ml), and the results obtained from untreated and compound treated cells are used to calculate an EC50 value. Selected compounds that have good activity against EBV VCA production without toxicity will be tested for their ability to inhibit EBV DNA synthesis.

For assays with HSV, the BHKICP6LacZ cell line, which was stably transformed with the *E. coli* lacZ gene under the transcriptional control of the HSV-1 UL39 promoter, can be used (See Stabell et al., 1992, Methods 38:195-204). Infected cells are detected using β-galactosidase assays known in the art, e.g., colorimetric assay.

Standard antiviral assays for influenza virus has been described, See, e.g., Sidwell et al., Antiviral Research, 2000, 48:1-16. These assays can also be adapted for use with other viruses.

4.3 Characterization of Safety and Efficacy of Compounds

The safety and efficacy of compounds can be assessed using technologies known to one of skill in the art. Sections 4.4 and 4.5 below provide non-limiting examples of cytotoxicity assays and animal model assays, respectively, to characterize the safety and efficacy of compounds. In certain embodiments, the cytotoxicity assays described in Section 4.4 are conducted following the in vitro antiviral assays described in Section 4, supra. In other embodiments, the cytotoxicity assays described in Section 4.4 are conducted before or concurrently with the in vitro antiviral assays described in Section 4, supra.

In some embodiments, compounds differentially affect the viability of uninfected cells and cells infected with virus. The differential effect of a compound on the viability of virally infected and uninfected cells may be assessed using techniques such as those described in Section 4.4, infra, or other techniques known to one of skill in the art. In certain embodiments, compounds are more toxic to cells infected with a virus than uninfected cells. In specific embodiments, compounds preferentially affect the viability of cells infected with a virus. Without being bound by any particular concept, the differential effect of a compound on the viability of uninfected and virally infected cells may be the result of the compound targeting a particular enzyme or protein that is differentially expressed or regulated or that has differential activities in uninfected and virally infected cells. For example, viral infection and/or viral replication in an infected host cells may alter the expression, regulation, and/or activities of enzymes and/or proteins. Accordingly, in some embodiments, other compounds that target the same enzyme, protein or metabolic pathway are examined for antiviral activity. In other embodiments, congeners of compounds that differentially affect the viability of cells infected with virus are designed and examined for antiviral activity. Non-limiting examples of antiviral assays that can be used to assess the antiviral activity of compound are provided in Section 4, supra.

4.4 Cytotoxicity Studies

In a preferred embodiment, the cells are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. Other non-limiting examples of cell lines that can be used to test the cytotoxicity of compounds are provided in Table 3.

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration (IC50) is determined by regression analysis of these data.

Compounds can be tested for in vivo toxicity in animal models. For example, animal models, described herein and/or others known in the art, used to test the antiviral activities of compounds can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound in accordance with the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided in Section 6.4, infra.

4.5 Animal Models

Compounds and compositions are preferably assayed in vivo for the desired therapeutic or prophylactic activity prior to use in humans. For example, in vivo assays can be used to determine whether it is preferable to administer a compound and/or another therapeutic agent. For example, to assess the use of a compound to prevent a viral infection, the compound can be administered before the animal is infected with the virus. In another embodiment, a compound can be administered to the animal at the same time that the animal is infected with the virus. To assess the use of a compound to treat or manage a viral infection, in one embodiment, the compound is administered after a viral infection in the animal. In another embodiment, a compound is administered to the animal at the same time that the animal is infected with the virus to treat and/or manage the viral infection. In a specific embodiment, the compound is administered to the animal more than one time.

Compounds can be tested for antiviral activity against virus in animal models systems including, but are not limited to, rats, mice, chicken, cows, monkeys, pigs, goats, sheep, dogs, rabbits, guinea pigs, etc. In a specific embodiment of the invention, compounds are tested in a mouse model system. Such model systems are widely used and well-known to the skilled artisan.

Animals are infected with virus and concurrently or subsequently treated with a compound or placebo. Samples obtained from these animals (e.g., serum, urine, sputum, semen, saliva, plasma, or tissue sample) can be tested for viral replication via well known methods in the art, e.g., those that measure altered viral replication (as determined, e.g., by plaque formation) or the production of viral proteins (as determined, e.g., by Western blot, ELISA, or flow cytometry analysis) or viral nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below (Sections 4.5.1-4.5.5) can be adapted for other viral systems.

The effect of a compound on the virulence of a virus can also be determined using in vivo assays in which the titer of the virus in an infected subject administered a compound, the length of survival of an infected subject administered a compound, the immune response in an infected subject administered a compound, the number, duration and/or severity of the symptoms in an infected subject administered a compound, and/or the time period before onset of one or more symptoms in an infected subject administered a compound is assessed. Techniques known to one of skill in the art can be used to measure such effects.

4.5.1 Herpes Simplex Virus (HSV)

Mouse models of herpes simplex virus type 1 or type 2 (HSV-1 or HSV-2) can be employed to assess the antiviral activity of compounds in vivo. BALB/c mice are commonly used, but other suitable mouse strains that are susceptible can also be used. Mice are inoculated by various routes with an appropriate multiplicity of infection of HSV (e.g., $10^5$ pfu of HSV-1 strain E-377 or $4 \times 10^4$ pfu of HSV-2 strain MS) followed by administration of compounds and placebo. For i.p. inoculation, HSV-1 replicates in the gut, liver, and spleen and spreads to the CNS. For i.n. inoculation, HSV-1 replicates in the nasopharynx and spreads to the CNS. Any appropriate route of administration (e.g., oral, topical, systemic, nasal), frequency and dose of administration can be tested to determine the optimal dosages and treatment regimens using compounds, optionally in combination with other therapies.

In a mouse model of HSV-2 genital disease, intravaginal inoculation of female Swiss Webster mice with HSV-1 or HSV-2 is carried out, and vaginal swabs are obtained to evaluate the effect of therapy on viral replication (See, e.g., Crute et al., Nature Medicine, 2002, 8:386-391). For example, viral titers by plaque assays are determined from the vaginal swabs. A mouse model of HSV-1 using SKH-1 mice, a strain of immunocompetent hairless mice, to study cutaneous lesions is also described in the art (See, e.g., Crute et al., Nature Medicine, 2002, 8:386-391 and Bolger et al., Antiviral Res., 1997, 35:157-165). Guinea pig models of HSV have also been described, See, e.g., Chen et al., Virol. J, 2004 Nov. 23, 1:11. Statistical analysis is carried out to calculate significance (e.g., a P value of 0.05 or less).

4.5.2 HCMV

Since HCMV does not generally infect laboratory animals, mouse models of infection with murine CMV (MCMV) can be used to assay antiviral activity compounds in vivo. For example, an MCMV mouse model with BALB/c mice can be used to assay the antiviral activities of compounds in vivo when administered to infected mice (See, e.g., Kern et al., Antimicrob. Agents Chemother., 2004, 48:4745-4753). Tissue homogenates isolated from infected mice treated or untreated with compounds are tested using standard plaque assays with mouse embryonic fibroblasts (MEFs). Statistical analysis is then carried out to calculate significance (e.g., a P value of 0.05 or less).

Alternatively, human tissue (i.e., retinal tissue or fetal thymus and liver tissue) is implanted into SCID mice, and the mice are subsequently infected with HCMV, preferably at the site of the tissue graft (See, e.g., Kern et al., Antimicrob. Agents Chemother., 2004, 48:4745-4753). The pfu of HCMV used for inoculation can vary depending on the experiment and virus strain. Any appropriate routes of administration (e.g., oral, topical, systemic, nasal), frequency and dose of administration can be tested to determine the optimal dosages and treatment regimens using compounds, optionally in combination with other therapies. Implant tissue homogenates isolated from infected mice treated or untreated with compounds at various time points are tested using standard plaque assays with human foreskin fibroblasts (HFFs). Statistical analysis is then carried out to calculate significance (i.e., a P value of 0.05 or less).

Guinea pig models of CMV to study antiviral agents have also been described, See, e.g., Bourne et al., Antiviral Res., 2000, 47:103-109; Bravo et al., Antiviral Res., 2003, 60:41-49; and Bravo et al, J. Infectious Diseases, 2006, 193:591-597.

4.5.3 Influenza

Animal models, such as ferret, mouse and chicken, developed for use to test antiviral agents against influenza virus have been described, See, e.g., Sidwell et al., Antiviral Res., 2000, 48:1-16; and McCauley et al., Antiviral Res., 1995, 27:179-186. For mouse models of influenza, non-limiting examples of parameters that can be used to assay antiviral activity of compounds administered to the influenza-infected mice include pneumonia-associated death, serum α1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or FIN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

4.5.4 Hepatitis

A HBV transgenic mouse model, lineage 1.3.46 (official designation, Tg[HBV 1.3 genome] Chi46) has been described previously and can be used to test the in vivo antiviral activities of compounds as well as the dosing and administration regimen (See, e.g., Cavanaugh et al., J. Virol., 1997, 71:3236-3243; and Guidotti et al., J. Virol., 1995, 69:6158-6169). In these HBV transgenic mice, a high level of viral replication occurs in liver parenchymal cells and in the proximal convoluted tubules in the kidneys of these transgenic mice at levels comparable to those observed in the infected liver of patients with chronic HBV hepatitis. HBV transgenic mice that have been matched for age (i.e., 6-10 weeks), sex (i.e., male), and levels of hepatitis B surface antigen (HBsAg) in serum can be treated with compounds or placebo followed by antiviral activity analysis to assess the antiviral activity of compounds. Non-limiting examples of assays that can be performed on these mice treated and untreated with compounds include Southern analysis to measure HBV DNA in the liver, quantitative reverse transcriptase PCR (qRT-PCR) to measure HBV RNA in liver, immunoassays to measure hepatitis e antigen (HBeAg) and HBV surface antigen (HBsAg) in the serum, immunohistochemistry to measure HBV antigens in the liver, and quantitative PCR (qPCR) to measure serum HBV DNA. Gross and microscopic pathological examinations can be performed as needed.

Various hepatitis C virus (HCV) mouse models described in the art can be used in assessing the antiviral activities of compounds against HCV infection (See Zhu et al., Antimicrobial Agents and Chemother., 2006, 50:3260-3268; Bright et al., Nature, 2005, 436:973-978; Hsu et al., Nat. Biotechnol., 2003, 21:519-525; Ilan et al., J. Infect. Dis. 2002, 185: 153-161; Kneteman et al., Hepatology, 2006, 43:1346-1353; Mercer et al., Nat. Med., 2001, 7:927-933; and Wu et al., Gastroenterology, 2005, 128:1416-1423). For example, mice with chimeric human livers are generated by transplanting normal human hepatocytes into SCID mice carrying a plasminogen activator transgene (Alb-uPA) (See Mercer et al., Nat. Med., 2001, 7:927-933). These mice can develop prolonged HCV infections with high viral titers after inoculation with HCV (e.g., from infected human serum). Thus, these mice can be administered a compound or placebo prior to, concurrently with, or subsequent to HCV infection, and replication of the virus can be confirmed by detection of negative-strand viral RNA in transplanted livers or expression of HCV viral proteins in the transplanted hepatocyte nodules. The statistical significance of the reductions in the viral replication levels are determined.

Another example of a mouse model of HCV involves implantation of the HuH7 cell line expressing a luciferase reporter linked to the HCV subgenome into SCID mice, subcutaneously or directly into the liver (See Zhu et al., Antimicrobial Agents and Chemother., 2006, 50:3260-3268). The mice are treated with a compound or placebo, and whole-body imaging is used to detect and quantify bioluminescence signal intensity. Mice treated with a compound that is effective against HCV have less bioluminescence signal intensity relative to mice treated with placebo or a negative control.

4.5.5 HIV

The safety and efficacy of compounds against HIV can be assessed in vivo with established animal models well known in the art. For example, a Trimera mouse model of HIV-1 infection has been developed by reconstituting irradiated normal BALB/c mice with murine SCID bone marrow and engrafted human peripheral blood mononuclear cells (See Ayash-Rashkovsky et al., FASEB J., 2005, 19:1149-1151). These mice are injected intraperitoneally with T- and M-tropic HIV-1 laboratory strains. After HIV infection, rapid loss of human $CD4^+$ T cells, decrease in CD4/CD8 ratio, and increased T cell activation can be observed. A compound can be administered to these mice and standard assays known in the art can be used to determine the viral replication capacity in animals treated or untreated with a compound. Non-limiting examples of such assays include the COBAS AMPLICOR® RT-PCR assay (Roche Diagnostics, Branchberg, N.J.) to determine plasma viral load (HIV-1 RNA copies/ml); active HIV-1 virus replication assay where human lymphocytes recovered from infected Trimera mice were cocultured with target T cells (MT-2 cells) and HIV-dependent syncytia formation was examined; and human lymphocytes recovered from infected Trimera mice were cocultured with cMAGI indicator cells, where HIV-1 LTR driven trans-activation of (3-galactosidase was measured. Levels of anti-HIV-1 antibodies produced in these mice can also be measured by ELISA. Other established mouse models described in the art can also be used to test the antiviral activity of compounds in vivo (See, Mosier et al., Semin. Immunol., 1996, 8:255-262; Mosier et al., Hosp. Pract. (Off Ed)., 1996, 31:41-48, 53-55, 59-60; Bonyhadi et al., Mol. Med. Today, 1997, 3:246-253; Jolicoeur et al., Leukemia, 1999, 13:S78-S80; Browning et al., Proc. Natl. Acad. Sci. USA, 1997, 94:14637-14641; and Sawada et al., J. Exp. Med., 1998, 187:1439-1449). A simian immunodeficiency virus (SIV) nonhuman primate model has also been described (See Schito et al., Curr. HIV Res., 2006, 4:379-386).

5. Pharmaceutical Compositions

Any compound described or incorporated by referenced herein may optionally be in the form of a composition comprising the compound.

In certain embodiments provided herein, compositions (including pharmaceutical compositions) comprise a compound and a pharmaceutically acceptable carrier, excipient, or diluent.

In other embodiments, provided herein are pharmaceutical compositions comprising an effective amount of a compound and a pharmaceutically acceptable carrier, excipient, or diluent. The pharmaceutical compositions are suitable for veterinary and/or human administration.

The pharmaceutical compositions provided herein can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP)SP(XXI)/NF (XVI). In general, lactose free compositions comprise an active ingredient, a binder/filler, and a lubricant in pharmaceutically compatible and pharmaceutically acceptable amounts. Preferred lactose free dosage forms comprise a compound, microcrystalline cellulose, pre gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a compound preferably in purified form, together with a suitable amount of carrier so as to provide the form for proper administration to the patient. The formulation should suit the mode of administration. In a preferred embodiment, the compositions or single unit dosage forms are sterile and in suitable form for administration to a subject, preferably an animal subject, more preferably a mammalian subject, and most preferably a human subject.

Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial, ophthalmic, and rectal administration. In a specific embodiment, the composition is formulated in accordance with routine procedures as a composition adapted for intravenous, subcutaneous, intramuscular, oral, intranasal, ophthalmic, or topical administration to human beings. In a preferred embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms provided herein are prepared by combining a compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Agents that increase the solubility of one or more of the compounds provided herein can also be incorporated into the parenteral dosage forms provided herein.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with a compound. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone);

urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more compounds. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of one or more compounds so as to improve delivery. In this regard, stearates can serve as a lipid vehicle for the formulation, as an emulsifying agent or surfactant, and as a delivery enhancing or penetration enhancing agent. Different salts, hydrates or solvates of the compounds can be used to further adjust the properties of the resulting composition.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

6. Prophylactic and Therapeutic Methods

The present invention provides methods of preventing, treating and/or managing a viral infection, said methods comprising administering to a subject in need thereof one or more compounds. In a specific embodiment, the invention provides a method of preventing, treating and/or managing a viral infection, said method comprising administering to a subject in need thereof a dose of a prophylactically or therapeutically effective amount of one or more compounds or a composition comprising a compound. A compound or a composition comprising a compound may be used as any line of therapy (e.g., a first, second, third, fourth or fifth line therapy) for a viral infection.

In another embodiment, the invention relates to a method for reversing or redirecting metabolic flux altered by viral infection in a human subject by administering to a human subject in need thereof, an effective amount of one or more compounds or a composition comprising one or more compounds. For example, viral infection can be treated using combinations of the enzyme inhibition compounds that produce beneficial results, e.g., synergistic effect; reduction of side effects; a higher therapeutic index.

In specific embodiments, a compound is the only active ingredient administered to prevent, treat, manage or ameliorate said viral infection. In a certain embodiment, a composition comprising a compound is the only active ingredient.

The present invention encompasses methods for preventing, treating, and/or managing a viral infection for which no antiviral therapy is available. The present invention also encompasses methods for preventing, treating, and/or managing a viral infection as an alternative to other conventional therapies.

The present invention also provides methods of preventing, treating and/or managing a viral infection, said methods comprising administering to a subject in need thereof one or more of the compounds and one or more other therapies (e.g., prophylactic or therapeutic agents). In a specific embodiment, the other therapies are currently being used, have been used or are known to be useful in the prevention, treatment and/or management of a viral infection. Non-limiting examples of such therapies are provided in Section 6, infra. In a specific embodiment, one or more compounds are administered to a subject in combination with one or more of the therapies described in Section 6, infra. In another embodiment, one or more compounds are administered to a subject in combination with a supportive therapy, a pain relief therapy, or other therapy that does not have antiviral activity.

The combination therapies of the invention can be administered sequentially or concurrently. In one embodiment, the combination therapies of the invention comprise a compound and at least one other therapy which has the same mechanism of action. In another embodiment, the combination therapies of the invention comprise a compound and at least one other therapy which has a different mechanism of action than the compound.

In a specific embodiment, the combination therapies of the present invention improve the prophylactic and/or therapeutic effect of a compound by functioning together with the compound to have an additive or synergistic effect. In another embodiment, the combination therapies of the present invention reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

6.1 Patient Population

According to the invention, compounds, compositions comprising a compound, or a combination therapy is administered to a subject suffering from a viral infection. In other embodiments, compounds, compositions comprising a compound, or a combination therapy is administered to a subject predisposed or susceptible to a viral infection. In some embodiments, compounds, compositions comprising a compound, or a combination therapy is administered to a subject that lives in a region where there has been or might be an outbreak with a viral infection. In some embodiments, the viral infection is a latent viral infection. In one embodiment, a compound or a combination therapy is administered to a human infant. In one embodiment, a compound or a combination therapy is administered to a premature human infant. In other embodiments, the viral infection is an active infection. In yet other embodiments, the viral infection is a chronic viral infection. Non-limiting examples of types of virus infections include infections caused by those provided in Section 4.1, supra.

In a specific embodiment, the viral infection is an enveloped virus infection. In some embodiments, the enveloped virus is a DNA virus. In other embodiments, the enveloped virus is a RNA virus. In some embodiments, the enveloped virus has a double stranded DNA or RNA genome. In other embodiments, the enveloped virus has a single-stranded DNA or RNA genome. In a specific embodiment, the virus infects humans.

In certain embodiments, a compound, a composition comprising a compound, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a compound, a composition comprising a compound, or a combination therapy is administered to a human at risk for a virus infection. In certain embodiments, a compound, a composition comprising a compound, or a combination therapy is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a compound, a composition comprising a compound, or a combination therapy is administered to a human infant. In other embodiments, a compound, or a combination therapy is administered to a human child. In other embodiments, a compound, a composition comprising a compound, or a combination therapy is administered to a human adult. In yet other embodiments, a compound, a composition comprising a compound, or a combination therapy is administered to an elderly human.

In certain embodiments, a compound, a composition comprising a compound, or a combination therapy is administered to a pet, e.g., a dog or cat. In certain embodiments, a compound, a composition comprising a compound, or a combination therapy is administered to a farm animal or livestock, e.g., pig, cows, horses, chickens, etc. In certain embodiments, a compound, a composition comprising a compound, or a combination therapy is administered to a bird, e.g., ducks or chicken.

In certain embodiments, a compound, a composition comprising a compound, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a compound, a composition comprising a compound, or a combination therapy is administered to a subject receiving or recovering from immunosuppressive therapy. In certain embodiments, a compound, a composition comprising a compound, or a combination therapy is administered to a subject that has or is at risk of getting cancer, AIDS, another viral infection, or a bacterial infection. In certain embodiments, a subject that is, will or has undergone surgery, chemotherapy and/or radiation therapy. In certain embodiments, a compound, a composition comprising a compound, or a combination therapy is administered to a subject that has cystic fibrosis, pulmonary fibrosis, or another disease which makes the subject susceptible to a viral infection. In certain embodiments, a compound, a composition comprising a compound, or a combination therapy is administered to a subject that has, will have or had a tissue transplant. In some embodiments, a compound, a composition comprising a compound, or a combination therapy is administered to a subject that lives in a nursing home, a group home (i.e., a home for 10 or more subjects), or a prison. In some embodiments, a compound, a composition comprising a compound, or a combination therapy is administered to a subject that attends school (e.g., elementary school, middle school, junior high school, high school or university) or daycare. In some embodiments, a compound, a composition comprising a compound, or a combination therapy is administered to a subject that works in the healthcare area, such as a doctor or a nurse, or in a hospital. In certain embodiments, a compound, a composition comprising a compound, or a combination therapy is administered to a subject that is pregnant or will become pregnant.

In some embodiments, a patient is administered a compound or a composition comprising a compound, or a combination therapy before any adverse effects or intolerance to therapies other than compounds develops. In some embodiments, compounds or compositions comprising one or more compounds, or combination therapies are administered to refractory patients. In a certain embodiment, refractory patient is a patient refractory to a standard antiviral therapy. In certain embodiments, a patient with a viral infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral infection is refractory when viral replication has not decreased or has increased.

In some embodiments, compounds or compositions comprising one or more compounds, or combination therapies are administered to a patient to prevent the onset or reoccurrence of viral infections in a patient at risk of developing such infections. In some embodiments, compounds or compositions comprising one or more compounds, or combination therapies are administered to a patient who are susceptible to adverse reactions to conventional therapies.

In some embodiments, one or more compounds or compositions comprising one or more compounds, or combination therapies are administered to a patient who has proven refractory to therapies other than compounds, but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered one or more compounds or compositions comprising one or more compounds, or combination therapies has not received a therapy prior to the administration of the compounds or compositions or combination therapies. In other embodiments, one or more compounds or compositions comprising one or more compounds, or combination therapies are administered to a subject who has received a therapy prior to administration of one or more compounds or compositions comprising one or more compounds, or combination therapies. In some embodiments, the subject administered a compound or a composition comprising a compound was refractory to a prior therapy or experienced adverse side effects to the prior therapy or the prior therapy was discontinued due to unacceptable levels of toxicity to the subject.

6.2 Mode of Administration

When administered to a patient, a compound is preferably administered as a component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as silastic membranes, or fibers. In such instances, administration may selectively target a local tissue without substantial release of a compound into the bloodstream.

In certain embodiments, it may be desirable to introduce a compound into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

For viral infections with cutaneous manifestations, the compound can be administered topically. Similarly, for viral infections with ocular manifestation, the compounds can be administered ocularly.

In another embodiment, a compound is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; See generally ibid.).

In another embodiment, a compound is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising a compound is placed in close proximity to the tissue infected with a virus to be prevented, treated and/or managed. In accordance with this embodiment, the close proximity of the controlled-release system to the infection may result in only a fraction of the dose of the compound required if it is systemically administered.

In certain embodiments, it may be preferable to administer a compound via the natural route of infection of the virus against which a compound has antiviral activity. For example, it may be desirable to administer a compound of the invention into the lungs by any suitable route to treat or prevent an infection of the respiratory tract by viruses (e.g., influenza virus). Pulmonary administration can also be employed, e.g., by use of an inhaler or nebulizer, and formulation with an aerosolizing agent for use as a spray.

6.3 Agents for Use in Combination with Compounds

Therapeutic or prophylactic agents that can be used in combination with compounds for the prevention, treatment and/or management of a viral infection include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, and non-steroidal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, buterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a viral infection or can be used in combination with compounds in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference ($61^{st}$ ed. 1007) for information regarding therapies (e.g., prophylactic or therapeutic agents) which have been or are currently being used for preventing, treating and/or managing viral infections.

6.3.1 Antiviral Agents

Antiviral agents that can be used in combination with compounds include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination compounds include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

6.3.2 Antibacterial Agents

Antibacterial agents, including antibiotics, that can be used in combination with compounds include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracycline, and analogs thereof. In some embodiments, antibiotics are administered in combination with a compound to prevent and/or treat a bacterial infection.

In a specific embodiment, compounds are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with compounds include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithromycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin, benethamine, penicillin O, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

6.4 Dosages and Frequency of Administration

The amount of a compound, or the amount of a composition comprising a compound, that will be effective in the prevention, treatment and/or management of a viral infection can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

In some embodiments, the dosage of a compound is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005. In one embodiment, a compound or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die (LD10). In general the starting dose of a Phase I clinical trial is based on preclinical testing. A standard measure of toxicity of a drug in preclinical testing is the percentage of animals that die because of treatment. It is well within the skill of the art to correlate the LD10 in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about 1/10 the murine LD10, although it may be even lower if other species (i.e., dogs) were more sensitive to the compound. In other embodiments, the standard conservative starting dose is about 1/100, 1/95, 1/90, 1/85, 1/80, 1/75, 1/70, 1/65, 1/60, 1/55, 1/50, 1/45, 1/40, 1/35, 1/30, 1/25, 1/20, 1/15, 2/10, 3/10, 4/10, or 5/10 of the murine LD10. In other embodiments, a starting dose amount of a compound in a human is lower than the dose extrapolated from animal model studies. In another embodiment, a starting dose amount of a compound in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of compounds or compositions include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In one embodiment, the dosage is a concentration of 0.01 to 5000 mM, 1 to 300 mM, 10 to 100 mM and 10 mM to 1 M. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM.

In one embodiment, the dosage is a concentration of 0.01 to 5000 mM, 1 to 300 mM, 10 to 100 mM and 10 mM to 1 M. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM. In a specific embodiment, the dosage is 0.25 µg/kg or more, preferably 0.5 µg/kg or more, 1 µg/kg or more, 2 µg/kg or more, 3 µg/kg or more, 4 µg/kg or more, 5 µg/kg or more, 6 µg/kg or more, 7 µg/kg or more, 8 µg/kg or more, 9 µg/kg or more, or 10 µg/kg or more, 25 µg/kg or more, preferably 50 µg/kg or more, 100 µg/kg or more, 250 µg/kg or more, 500 µg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 mg, about 150 mg to about 300 mg, about 150 mg to about 400 mg, 250 mg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a compound, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound of the invention by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of a compound or a composition, wherein the prophylactically or therapeutically effective amount is not the same for each dose. In another embodiment, a subject is administered one or more doses of a prophylactically or therapeutically effective amount of a compound or a composition, wherein the dose of a prophylactically or therapeutically effective amount administered to said subject is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses. In another embodiment, a subject is administered one or more doses of a prophylactically or therapeutically effective amount of a compound or composition, wherein the dose is decreased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses.

In certain embodiments, a subject is administered a compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral genome replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments, a subject is administered a compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral protein synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a compound or a composition in an amount effective to inhibit or reduce viral infection by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce viral infection by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a compound or a composition in an amount effective to inhibit or reduce viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce viral replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a compound or a composition in an amount effective to inhibit or reduce viral replication by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a compound or a composition in an amount effective to inhibit or reduce the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments, a dose of a compound or a composition is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of a viral infection can be determined using references available to a clinician such as, e.g., the Physicians' Desk Reference ($61^{st}$ ed. 2007). Preferably, dosages lower than those which have been or are currently being used to prevent, treat and/or manage the infection are utilized in combination with one or more compounds or compositions.

For compounds which have been approved for uses other than prevention, treatment or management of viral infections, safe ranges of doses can be readily determined using references available to clinicians, such as e.g., the Physician's Desk Reference ($61^{st}$ ed. 2007).

The above-described administration schedules are provided for illustrative purposes only and should not be considered limiting. A person of ordinary skill in the art will readily understand that all doses are within the scope of the invention.

It is to be understood and expected that variations in the principles of invention herein disclosed may be made by one skilled in the art and it is intended that such modifications are to be included within the scope of the present invention.

Throughout this application, various publications are referenced in parentheses. The disclosures of these publications in their entireties are hereby incorporated by reference into this application to more fully describe the state of the art to which this invention pertains. The following examples further illustrate the invention, but should not be construed to limit the scope of the invention in any way.

EXAMPLES

Example 1

Impact of HCMV on Global Glycerol Phospholipids

Serum-starved, confluent fibroblasts (approximately $2.1 \times 10^6$ cells) were infected at a multiplicity of infection (MOI) of 3 $TCID_{50}$ units/ml with laboratory strain, bacterial artificial chromosome (BAC)-derived AD169 wild-type strain of HCMV (BADWT). Samples were collected over a 96-h time course and chloroform-methanol extracted for lipids at specific time points. Samples were chilled at −80° C. and analyzed by liquid chromatography mass spectrometry analysis.

Phospholipids were extracted from control and HCMV-infected cells or purified virion samples by a modified Bligh and Dyer extraction using acidified methanol. Approximately $2\times10^6$ cells (or $1\text{-}8\times10^8$ $TCID_{50}$ of purified virion) were washed twice with 1 ml cold 1×PBS and the PBS was aspirated. Cells were then scraped in 800 μL of ice-cold 0.1 N HCl:methanol (1:1) and transferred into a cold microfuge tube. After addition of 400 μL of ice-cold $CHCl_3$, samples were vortexed for 1 minute at 4° C. and layers were separated by centrifugation (18,000 g for 5 min, 4° C.). The lower organic layer was isolated, mass spectrometry standards were added and solvent was evaporated. The resulting lipid film was dissolved in 100 μl of isopropanol (IPA):hexane:100 mM $NH_4COOH_{(aq)}$ 58:40:2 (mobile phase A). The mass spectrometric analysis and quantitation were performed essentially as described in Ivanova et al., Methods Enzymol, 2007, 432, 21-57. LC-MS techniques were used with the utilization of synthetic odd-carbon phospholipid standards (four per each phospholipid class). MDS SCIEX 4000QTRAP hybrid triple quadrupole/linear ion trap mass spectrometer (Applied Biosystems, Foster City, Calif.) was used for the analyses. Coupled to it was a Shimadzu HPLC system (Shimadzu Scientific Instruments, Inc., Columbia, Md.) consisting of an SCL 10 APV controller, two LC 10 ADVP pumps and a CTC HTC PAL autosampler (Leap Technologies, Carrboro, N.C.). Phospholipids were separated on a Phenomenex Luna silica column (Phenomenex, Torrance, Calif.) (2×250 mm, 5μ particle size) using a 20 μL sample injection. A binary gradient consisting of IPA:hexane:100 mM $NH_4COOH_{(aq)}$ 58:40:2 (mobile phase A) and IPA:hexane:100 mM $NH_4COOH_{(aq)}$ 50:40:10 (mobile phase B) was used for the separation. The 100 mM $NH_4COOH_{(aq)}$ 50:40:10 (mobile phase B) was used for the separation. The parameters of the mass spectrometer instrument and solvent gradient were as described in Ivanova et al., Methods Enzymol, 2007, 432, 21-57.

The analysis monitored 146 different glycerol phospholipids (GPs) over the HCMV life cycle. Of the 146 measured species, the major GP classes (phosphatidylcholine (PC), phosphatidylethanolamine (PE), phosphatidylserine (PS)) generally showed less than two-fold changes compared to mock over time, and none showed greater than a five-fold change versus mock. Of the changes that were observed, the most obvious changes were absolute increases in saturated and monounsaturated phosphatidic acid (PA) species.

Example 2

Inhibition of HCMV Replication by GPAT-Specific RNA Interference

Short-hairpin interfering RNA (shRNA) technology was used to knock down expression of mitochondrial GPAT (GPAM). Plasmids that express selected shRNA were used to develop lentiviruses which were transduced into fibroblasts. Mission shRNA bacterial glycerol stocks (NM_020918 Sigma-Aldrich) were cultured and purified shRNA-containing plasmids against GPAT were prepared. 10 μg of purified shRNA containing plasmid and necessary lentivirus packaging plasmids were then transfected into human embryonic kidney 293T cells with FuGene reagent (Roche). Cells were then placed at 32° C., and lentiviral particles were harvested. Human foreskin fibroblasts (HFFs) were then transduced with packaged lentiviruses and puromycin selected for shRNA expression.

Puromycin-resistant fibroblasts were established that expressed short-hairpin RNAs against mitochondrial GPAT mRNA transcripts. The shRNAs were CCGGGCTGCT-GAATTAAACCCTGATCTCGAGAT-CAGGGTTTAATTCAGCAGCTTTTTG (SEQ ID NO:1), CCGGGCTGGGAAATTGTGTCACAATCTC-GAGATTGTGACACAATTTCCCAGCTTTTTG (SEQ ID NO:2), and CCGGGCAAGCGTTGTTACCAGCTATCTC-GAGATAGCTGGTAACAACGCTTGCTTTTTG (SEQ ID NO:3), designated "39," "42," and "43," respectively. A control cell line expressing a non-targeting shRNA was also established. These cell lines were then infected at an MOI of 0.1 $TCID_{50}$ units/ml, 1.0 $TCID_{50}$ units/ml, or 3.0 $TCID_{50}$ units/ml and cell-free supernatants were harvested at 0, 4 and 9 days post infection. Harvested supernatants were then titered by $TCID_{50}$ analysis. FIG. 1 shows noticeable decreases in HCMV viral titer in knockdown cell lines when compared to a cell line transduced with a non-targeting shRNA plasmid.

Example 3

Dose-Dependent Inhibition of HCMV Replication by Inhibition of GPAT

Figure 2:
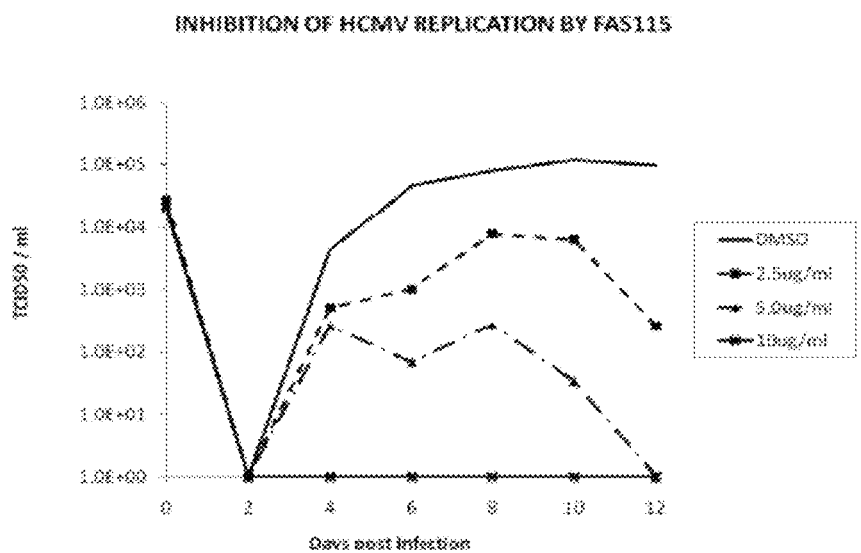
FIG. 2. Inhibition of HCMV Replication by Inhibition of GPAT. Serum-starved fibroblasts were infected with HCMV at a multiplicity of 0.1 $TCID_{50}$ units per cell. After adsorption for 1 h, cultures were re-fed with serum-free medium containing concentrations of 2.5 µg/ml, 5 µg/ml and 10 µg/ml of FAS 115 or with DMSO, the solvent used to dissolve FAS 115. Medium was assayed at 0, 2, 4, 6, 8, 10 and 12 days after infection and the production of infectious progeny was determined by $TCID_{50}$ assay on fibroblasts.

Serum-starved fibroblasts were infected with HCMV at a multiplicity of 0.1 $TCID_{50}$ units per cell. After adsorption for 1 h, cultures were re-fed with serum-free medium containing concentrations of 2.5μ/ml, 5μ/ml and 10μ/ml of FAS 115 or with DMSO, the solvent used to dissolve FAS 115. The medium was assayed at 0, 2, 4, 6, 8, 10 and 12 days after infection and the production of infectious progeny was determined by $TCID_{50}$ assay on fibroblasts. At the lowest FAS 115 concentration, viral titers were reduced by about an order of magnitude. At the highest concentration, production of virus was not observed on day 12 after infection. (FIG. 2).

Example 4

Inhibition of GPAT Reduces Expression of HCMV Late Proteins

Serum-starved fibroblasts were infected with human cytomegalovirus at a multiplicity of 3.0 $TCID_{50}$ units/cell.

Figure 3:
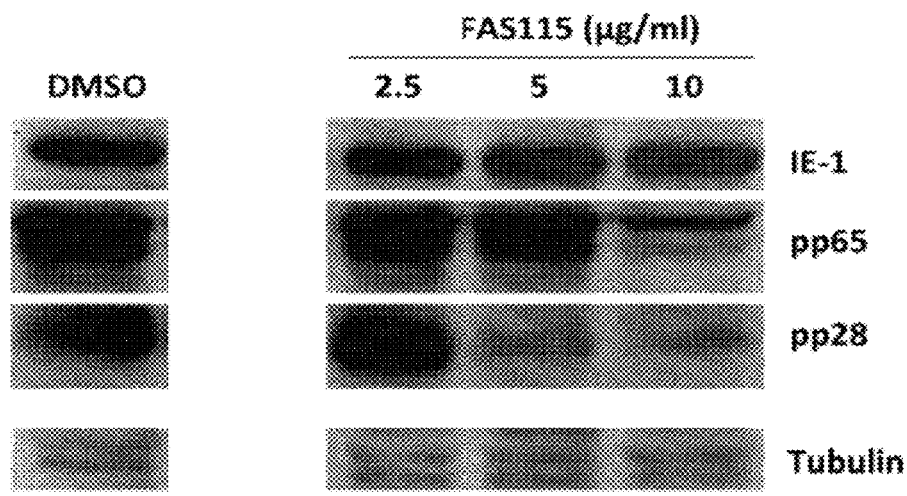
FIG. 3. Dose-dependent Inhibition of Human Cytomegalovirus Late Protein Expression by Inhibition of GPAT. Serum-starved fibroblasts were infected with human cytomegalovirus at a multiplicity of 3.0 $TCID_{50}$ units/cell. After adsorption for 1 h, cultures were re-fed with serum-free medium containing the indicated concentrations of FAS 115 or with DMSO, the solvent used to dissolve FAS 115. Cells were harvested at 96 hours after infection and viral protein expression was assessed by Western blot. IE-1 is a viral protein expressed immediately early during infection. pp65 and pp28 are viral proteins expressed late during HCMV infection. Tubulin is a loading control.

After adsorption for 1 h, cultures were re-fed with serum-free medium containing 2.5µ/ml, 5µ/ml and 10µ/ml of FAS 115 or with DMSO, the solvent used to dissolve FAS 115. Cells were harvested at 96 hours after infection and viral protein expression was assessed by Western blot. IE-1 is a viral protein expressed during the immediate-early phase of infection. pp65 and pp28 are viral proteins expressed late during HCMV infection. Tubulin is a loading control. As compared to a cellular protein control (tubulin) and an immediate early HCMV protein (IE-1), expression of pp65 and pp28 were noticeably reduced at the intermediate and high concentrations of FAS 115. (FIG. 3).

Example 5

Dose-Dependent Inhibition of HSV-1 Replication by Inhibition of GPAT

Figure 4:
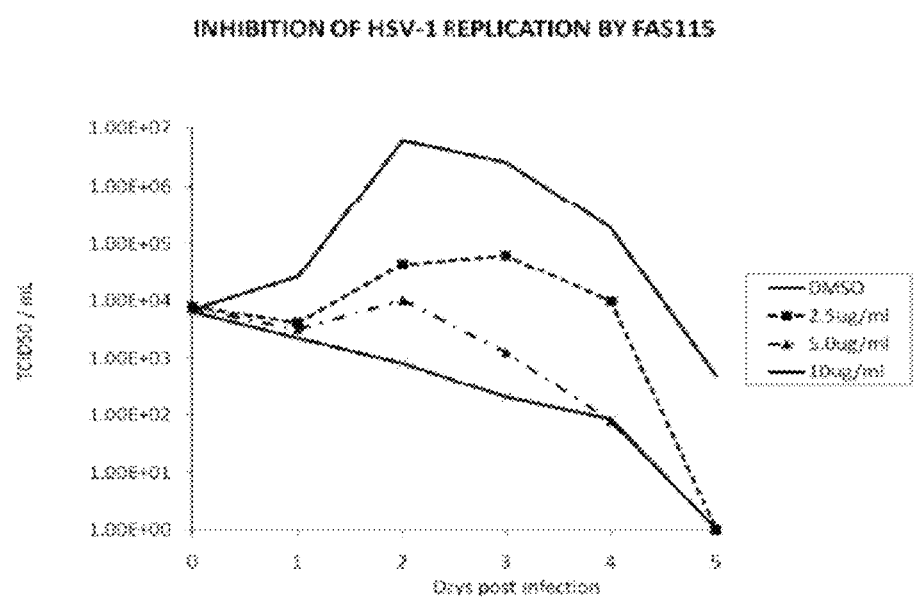
FIG. 4. Dose-dependent Inhibition of Herpes Simplex Virus-1 Replication by Inhibition of GPAT. Serum-starved fibroblasts were infected with herpes simplex virus-1 at a multiplicity of 0.01 TCID50 units/cell. After adsorption for 1 h, cultures were re-fed with serum-free medium containing the indicated concentrations of FAS 115 or with DMSO, the solvent used to dissolve FAS 115. Medium was harvested at the indicated times after infection and the production of infectious progeny was determined by TCID50 assay on fibroblasts.

Serum-starved fibroblasts were infected with herpes simplex virus-1 at a multiplicity of 0.01 $TCID_{50}$ units/cell. After adsorption for 1 h, cultures were re-fed with serum-free medium containing concentrations of 2.5µ/ml, 5µ/ml and 10µ/ml of FAS 115 of FAS 115 or with DMSO, the solvent used to dissolve FAS 115. The medium was assayed daily for five days and the production of infectious progeny was determined by $TCID_{50}$ assay on fibroblasts. At the lowest FAS 115 concentration, HSV-1 replication was reduced and viral titers were about an order of magnitude lower than in untreated cells. At higher concentrations, the concentration of infectious virus was reduced to 1 $TCID_{50}$ unit/ml or less after 5 days. (FIG. 4).

Example 6

Methods

Cell Lines, Viral Stock. Low passage fibroblasts (passage 6-8) were cultured in a medium containing 10% fetal bovine serum. Bacterial artificial chromosome-derived HCMV AD 169 strain (BADWT) was propagated in human foreskin fibroblasts (HFFs), concentrated via a 20% sorbitol cushion, and resuspended as a stock in serum-free media.

We claim:

1. A method of treating a viral infection in a mammal, comprising administering to a mammalian subject in need thereof a therapeutically effective amount of a compound or prodrug thereof, or pharmaceutically acceptable salt or ester of said compound or prodrug wherein the compound is compound of Formula I:

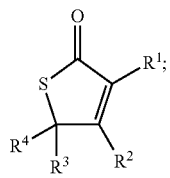

wherein
  $R^1$ and $R^2$ are each independently —H, —OH, —OR$^5$, —OCH$_2$C(O)R$^5$, —OCH$_2$C(O)NHR$^5$, —OC(O)R$^5$, —OC(O)OR$^5$, —OC(O)NHNH—R$^5$, —OC(O)NR$^5$R$^6$, C$_1$-C$_{20}$ alkyl, cycloalkyl, alkenyl, alkynyl, aryl, arylalkyl, alkylaryl, —CHR$^5$OR$^6$, —CO(O)R$^5$, —C(O)NR$^5$R$^6$, —CH$_2$C(O)R$^5$, —CH$_2$C(O)NHR$^5$, —C(O)R$^5$, —CH$_2$OR$^5$, —C(O)R$^5$, —CO(O)R$^5$, —C(O)NR$^5$R$^6$, —CH$_2$C(O)R$^5$, or —CH$_2$C(O)NHR$^5$,
  $R^5$ and $R^6$ are each independently H, C$_1$-C$_{20}$ alkyl, cycloalkyl, alkenyl, alkynyl, aryl, arylalkyl, alkylaryl, or optionally contain halogen atoms;
  $R^3$ and $R^4$, the same or different from each other, are C$_1$-C$_{20}$ alkyl, cycloalkyl, alkenyl, alkynyl, aryl, arylalkyl, or alkylaryl; and
wherein the viral infection is by an enveloped virus.

2. The method of claim 1, which further comprises administering a second compound or prodrug thereof, or pharmaceutically acceptable salt or ester of said compound or prodrug that inhibits a phosphatidic acid synthesis enzyme.

3. The method of claim 1, further comprising administering to the mammalian subject an inhibitor of acetyl-CoA carboxylase (ACC), an inhibitor of a long chain acyl-CoA synthase, an inhibitor of an elongase, an inhibitor of HMG-CoA reductase, or an inhibitor of mTOR.

4. The method of claim 1, wherein the compound is

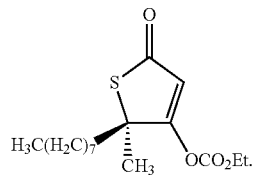

5. The method of claim 1, wherein the enveloped virus is human cytomegalovirus (HCMV).

6. The method of claim 1, wherein the enveloped virus is herpes simplex virus-1 (HSV-1).

* * * * *

SEQUENCE LISTING

```
<160> NUMBER OF SEQ ID NOS: 3

<210> SEQ ID NO 1
<211> LENGTH: 58
<212> TYPE: DNA
<213> ORGANISM: Artificial
<220> FEATURE:
<223> OTHER INFORMATION: encodes shRNA

<400> SEQUENCE: 1
ccgggctgct gaattaaacc ctgatctcga gatcagggtt taattcagca gcttttg        58

<210> SEQ ID NO 2
<211> LENGTH: 58
<212> TYPE: DNA
<213> ORGANISM: Artificial
<220> FEATURE:
<223> OTHER INFORMATION: encodes shRNA

<400> SEQUENCE: 2
ccgggctggg aaattgtgtc acaatctcga gattgtgaca caatttccca gcttttg        58

<210> SEQ ID NO 3
<211> LENGTH: 58
<212> TYPE: DNA
<213> ORGANISM: Artificial
<220> FEATURE:
<223> OTHER INFORMATION: encodes shRNA

<400> SEQUENCE: 3
ccgggcaagc gttgttacca gctatctcga gatagctggt aacaacgctt gcttttg        58
```